(12) United States Patent
Childress

(10) Patent No.: US 12,311,066 B2
(45) Date of Patent: May 27, 2025

(54) ULTRAVIOLET LIGHT SANITIZING SYSTEM AND METHOD WITH OCCUPANCY DETECTION

(71) Applicant: THE BOEING COMPANY, Chicago, IL (US)

(72) Inventor: Jamie J. Childress, Mercer Island, WA (US)

(73) Assignee: THE BOEING COMPANY, Chicago, IL (US)

( * ) Notice: Subject to any disclaimer, the term of this patent is extended or adjusted under 35 U.S.C. 154(b) by 761 days.

(21) Appl. No.: 17/455,106

(22) Filed: Nov. 16, 2021

(65) Prior Publication Data

US 2022/0184253 A1 Jun. 16, 2022

Related U.S. Application Data

(60) Provisional application No. 63/124,402, filed on Dec. 11, 2020.

(51) Int. Cl.
*A61L 2/10* (2006.01)

(52) U.S. Cl.
CPC ..................................... *A61L 2/10* (2013.01)

(58) Field of Classification Search
CPC .... A61L 2/10; A61L 2202/14; A61L 2202/25; A61L 2/24
See application file for complete search history.

(56) References Cited

U.S. PATENT DOCUMENTS

| | | | |
|---|---|---|---|
| 10,195,300 B2 | 2/2019 | Lloyd | |
| 10,847,009 B1 | 11/2020 | Sulucz et al. | |
| 2008/0067418 A1* | 3/2008 | Ross | A61L 2/24 250/455.11 |
| 2016/0250362 A1* | 9/2016 | Mackin | B64D 11/06 244/118.5 |
| 2016/0296649 A1* | 10/2016 | Ramanand | A61L 2/10 |
| 2017/0246331 A1* | 8/2017 | Lloyd | A61Q 17/04 |

(Continued)

FOREIGN PATENT DOCUMENTS

| | | |
|---|---|---|
| WO | 2021225951 A1 | 11/2021 |
| WO | 2022039957 A1 | 2/2022 |

OTHER PUBLICATIONS

Office Action received for related EP App.: 21208602.9 dated Jul. 26, 2023 (5 pages).

(Continued)

*Primary Examiner* — Regina M Yoo

(74) *Attorney, Agent, or Firm* — Philip S. Hof; The Small Patent Law Group LLC

(57) ABSTRACT

A system and method for sanitizing a target zone include an infrared (IR) sensor, a control unit, and one or more ultraviolet (UV) lamps. The IR sensor is configured to generate thermal image data of a target zone within a space. The control unit includes one or more processors and is communicatively connected to the IR sensor and the one or more UV lamps. The control unit is configured to determine an occupancy status of the target zone based on the thermal image data and a reference temperature of the space. Each of the one or more UV lamps is configured to emit UV light into the target zone. The control unit is configured to operate the one or more UV lamps based on the determined occupancy status of the target zone.

20 Claims, 10 Drawing Sheets

(56) References Cited

U.S. PATENT DOCUMENTS

| | | | | |
|---|---|---|---|---|
| 2018/0064833 | A1* | 3/2018 | Childress | B64D 11/02 |
| 2018/0339075 | A1* | 11/2018 | Kennedy | A61L 2/24 |
| 2020/0147249 | A1 | 5/2020 | Hussein et al. | |
| 2020/0179543 | A1* | 6/2020 | Deshays | A61L 2/24 |
| 2021/0077651 | A1* | 3/2021 | Romo | A61L 2/10 |
| 2021/0361810 | A1* | 11/2021 | Glanz | A61L 2/24 |
| 2022/0008607 | A1* | 1/2022 | Blaevoet | A61L 9/20 |
| 2022/0062463 | A1* | 3/2022 | Ramer | F24F 8/22 |
| 2022/0062475 | A1* | 3/2022 | Johnson | A61L 2/22 |
| 2022/0067377 | A1* | 3/2022 | Park | G06V 40/10 |
| 2022/0087498 | A1* | 3/2022 | Madden | A47L 9/2805 |
| 2022/0113006 | A1* | 4/2022 | Childress | A61L 2/10 |
| 2022/0160918 | A1* | 5/2022 | Beck | H04N 13/254 |
| 2022/0341609 | A1* | 10/2022 | McNamara | G16H 15/00 |
| 2022/0370671 | A1* | 11/2022 | Starkweather | G16H 40/20 |

OTHER PUBLICATIONS

Taha, et al. "Design of an Occupancy Monitoring Unit: A Thermal Imaging Based People Counting Solution for Socio-Technical Energy Saving Systems in Hospitals", 2019 11th Computer Science and Electronic Engineering (CEEC), IEEE, Sep. 18, 2019 (6 pages).

European Search Report received for related European Patent Application No. 21 20 8602 dated Apr. 26, 2022 (8 pages).

* cited by examiner

ULTRAVIOLET LIGHT SANITIZING SYSTEM AND METHOD WITH OCCUPANCY DETECTION

CROSS-REFERENCE TO RELATED APPLICATIONS

This application relates to and claims priority benefits from U.S. Provisional Patent Application No. 63/124,402, filed Dec. 11, 2020, which is hereby incorporated by reference in its entirety.

FIELD OF THE DISCLOSURE

Embodiments of the present disclosure generally relate to ultraviolet (UV) light sanitizing systems, such as UV light sanitizing systems that may be used to sanitize structures and areas within vehicles.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

A UV light sanitizing system typically includes at least one UV lamp that emits UV light. Some UV light sanitizing systems are installed within a space, and the UV lamp directs the UV light into the space to sanitize or disinfect one or more components within the space. The space may be periodically occupied, such that people may enter the space for various periods of time. Detection of occupants in the space by the system is a consideration for whether to operate the UV light sanitizing system and/or selecting operational parameters (e.g., time) for the UV light sanitizing system. Most known methods of occupancy detection rely on a changing environment or scene characterized by movement. For example, some sensors detect occupancy based on a person passing through a laser beam that extends across a threshold. Other sensors, such as cameras that generate visible image data and/or infrared (IR) (or thermal) image data, determine occupancy based on detected changes in the field of view. For example, existing passive IR sensors use differential IR over broad areas and register motion as occupancy detection via the differential IR of a moving object.

A drawback to the occupancy detection systems that rely on a motion is that the systems may incorrectly classify an occupied space as unoccupied when the environment is relatively static (e.g., unchanging). For example, there are various scenarios in which a person may be relatively still or stationary for an extended period of time, such as if the person is asleep, reading, watching a video, waiting to access or exit a room, or the like. The known occupancy detection systems may initially detect occupation when the person was active, but over time the unchanging scene becomes normalized and occupancy is no longer detected. After an incorrect classification of a space as unoccupied, the UV sanitizing system may activate the at least one UV lamp to emit UV light into the space.

Furthermore, certain rooms that have installed UV light sanitizing systems are configured to immediately deactivate the UV lamp upon detection of one or more persons within the room to preclude the one or more persons from receiving a dose of UV light. Even if the occupancy of the room is transient, the UV lamp is automatically controlled to stop emitting UV light, or to reduce the power output of the UV light to a very low, nominal level. In rooms or spaces that are periodically occupied, such drastic responses to occupation may interfere with the disinfection of the components within the rooms or spaces by reducing the UV dose administered to the components and extending the time required to reach a certain predetermined UV dose.

SUMMARY OF THE DISCLOSURE

A need exists for a UV light sanitizing system and method with accurate occupancy detection of a space, even in static, non-changing environments. A need also exists for dynamic disinfection of periodically occupied rooms and spaces, where the irradiance of the UV light is modulated based on the occupancy of the rooms and spaces. For example, the irradiance may be modified in response to persistent occupation of a room, but not modified in response to transient occupation of the room.

With that need in mind, certain embodiments of the present disclosure provide a sanitizing system that includes an infrared (IR) sensor, a control unit, and one or more ultraviolet (UV) lamps. The IR sensor is configured to generate thermal image data of a target zone within a space. The control unit includes one or more processors and is communicatively connected to the IR sensor and the one or more UV lamps. The control unit is configured to determine an occupancy status of the target zone based on the thermal image data and a reference temperature of the space. Each of the one or more UV lamps is configured to emit UV light into the target zone. The control unit is configured to operate the one or more UV lamps based on the determined occupancy status of the target zone.

Certain embodiments of the present disclosure provide a sanitizing method that includes receiving, at a control unit including one or more processors, thermal image data generated by an infrared (IR) sensor and associated with a target zone within a space. The method includes determining, via the control unit, an occupancy status of the target zone based on the thermal image data and a reference temperature of the space. The method also includes operating one or more ultraviolet (UV) lamps, via the control unit, based on the occupancy status of the target zone. The one or more UV lamps are configured to emit UV light into the target zone.

Certain embodiments of the present disclosure provide a sanitizing system that includes an infrared (IR) sensor, a control unit, and one or more ultraviolet (UV) lamps. The IR sensor is configured to generate thermal image data of a target zone within a space. The IR sensor is calibrated such that the thermal image data indicates an absolute temperature of one or more components in the target zone. The control unit includes one or more processors and is communicatively connected to the IR sensor and the one or more UV lamps. The control unit is configured to (i) determine an ambient temperature of the space based on sensor data generated by the IR sensor or a second sensor, (ii) determine a threshold temperature based on the ambient temperature of the space, and (iii) determine an occupancy status of the target zone by comparing the absolute temperature of the one or more components to the threshold temperature. Each of the one or more UV lamps is configured to emit UV light into the target zone. The control unit is configured to operate the one or more UV lamps based on the occupancy status of the target zone.

DETAILED DESCRIPTION OF THE DISCLOSURE

Figure 1:
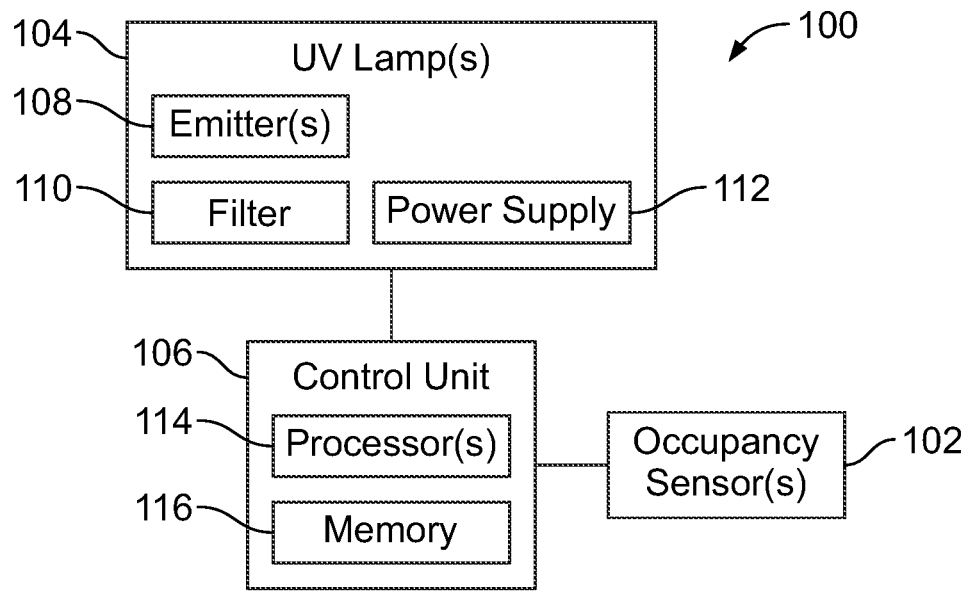
FIG. 1 illustrates a schematic block diagram of a sanitizing system for disinfecting one or more components within a space, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method for sanitizing (for example, disinfecting, decontaminating, cleaning, or the like) one or more components within a space. The system includes one or more UV lamps, one or more sensors for occupancy detection, and a control unit having one or more processors. The control unit is communicatively connected to the one or more UV lamps and the one or more sensors. The sanitizing system and method provide accurate occupancy detection of the space, even in static, non-changing environments over an extended period of time. At least one sensor in the system is an infrared (IR) sensor that monitors a target zone in a space.

The target zone represents an area or region that is occasionally occupied by one or more people. The IR sensor may monitor the target zone by generating thermal image data corresponding to, or associated with, the target zone. The IR sensor is calibrated such that the thermal image data represents the absolute temperature of one or more components (e.g., objects and structures) within the target zone.

In one or more embodiments, the sanitizing system and method are configured to determine occupancy using the absolute temperature of the one or more components within the target zone and a reference temperature. The reference temperature may be an ambient temperature in the space. The reference temperature may represent the measured temperature of a non-target zone in the space. The non-target zone may be predetermined or known as being unoccupied, such as an area of the ceiling or another area that is not accessible to, or at least not accessed by, people. The sanitizing system and method compare the absolute temperature to a threshold temperature to determine occupancy. For example, if the absolute temperature of a component in the target zone is above the threshold temperature, the target zone is determined to be occupied. Inversely, if the absolute temperature of the component is not above the threshold temperature, the target zone is determined to be unoccupied. The threshold temperature may vary based on the reference temperature. For example, the reference temperature may be used to determine (e.g., select, calculate, look up, etc.) the threshold temperature. The threshold temperature may be periodically updated over time based on monitored changes in the reference temperature. Determining and updating the threshold temperature over time based on the reference temperature allows the sanitizing system to constantly calibrate and retain IR detection even for a non-changing environment with one or more stationary occupants.

The threshold temperature is adjusted based on the reference temperature because the reliability of the absolute temperature measurement by the IR sensor may vary depending on the ambient environment. The threshold temperature may be based on or calibrated using expected skin temperature of a human. The skin temperature of a person is affected by the ambient temperature. For example, in a cool environment, the skin temperature of a human will be lower than the skin temperature in a hot environment. Hypothetically, a threshold temperature set to 85° F. would work well if the ambient temperature in the environment is 70° F., because generally non-living objects in the environment would have absolute temperatures close to 70° F. (below the threshold), while living objects such as people in the environment would have absolute temperatures close to 98° F. (above the threshold). However, that same 85° F. threshold would not be as useful if the ambient temperature is at or above 85° F., because non-living objects in the zone could trigger an occupancy detection, even without an actual occupant present, based on the heating of the objects in the hot ambient environment. Such a situation may result in a false positive occupation status, indicating that a space is occupied although the space is actually not occupied. Conversely, if the threshold temperature is 85° F. and the ambient temperature in the space is 40° F., the skin temperature of a person may drop below the 85° F. threshold, which may result in a false negative occupation status. The false negative indicates that the space is unoccupied although the space is actually occupied. The sanitizing system and method disclosed herein adjust or modulate the threshold temperature based at least on the reference temperature in the space to increase the accuracy of the occupancy determination, avoiding false negatives and false positives, regardless of movement in the environment.

In one or more embodiments, the sanitizing system and method are configured such an output level of the UV light emitted by the one or more UV lamps is modulated based on the occupancy of the target zone in the space. The output level may refer to intensity (e.g., brightness) or irradiance of the UV light. The irradiance may refer to the radiant flux (e.g., power) received by a surface per unit area, which can be measured in units of milliwatt per square centimeter ($mW/cm^2$). In one or more embodiments, the output level of the UV light is modulated such that the UV light has a full irradiance level when the target zone is unoccupied. Operating at the full irradiance level provides a high disinfection dose to one or more components in the target zone. The system modulates the UV light by reducing and varying the irradiance of the UV light in response to periodic occupation of the target zone by one or more people. For example, the system may gradually reduce the irradiance level of the UV light, in discrete steps or in a continuous slide, during a period of persistent occupation of the target zone. Eventually, the system may deactivate the UV lamp to stop emitting UV light or may continuously emit UV light at a low irradiance level that is safe for human tissues at extended periods of exposure.

FIG. 1 illustrates a schematic block diagram of a sanitizing system 100 for disinfecting one or more components within a space, according to an embodiment of the present disclosure. The one or more components can represent any objects or structures to be disinfected with UV light. For example, a component can be a structure within a vehicle, a fixed building, or the like. As an example, the component can be a passenger seat within a vehicle, a portion of a lavatory (such as a toilet, sink, door handle, and/or the like), a counter or other such surface within a kitchen or galley, and/or the like.

The sanitizing system 100 includes one or more UV lamps 104. The UV lamps 104 are positioned and configured to emit UV light into a target zone within a space for sanitizing or disinfecting one or more components within the target zone. Each UV lamp 104 includes one or more UV emitters 108 that generate the UV light. For example, the UV lamps 104 may have multiple UV emitters 108. The UV emitters 108 are held by respective enclosures or housings of the UV lamps 104.

In a non-limiting example, at least some of the UV emitters 108 are excimer emitters that have a gas enclosed in a tube. The gas may include or represent a noble gas, such as krypton chloride (KrCl). The UV emitters 108 may operate by receiving high voltage, high frequency electrical energy, which excites the gas. The gas releases excitation energy in the form of UV photons. The UV emitters 108 may be configured to emit UV light a far UV light spectrum and/or a UV-C spectrum. For example, the UV emitters 108 can emit UV light within the far UV spectrum, such as from 200 nanometers (nm) to 230 nm, and/or within the UV-C spectrum, such as from 230 nm to 280 nm. For example, the UV light emitters can emit UV light at 222 nm. As another example, the UV light emitters 108 can emit UV light at 254 nm. The UV emitters 108 may emit UV light at a narrow wavelength range centered about a designated wavelength, such as 222 nm. In a non-limiting example, the UV emitters 108 may be excimer emitters, such as KrCl excimer emitters. Optionally, some of the UV lamps 104 may have different types of UV emitters relative to one another. Various types of UV emitters 108 and UV lamps 104 may be utilized in the sanitizing system 100.

The UV lamps 104 optionally may include one or more wavelength selective filters 110 configured to block emission of one or more wavelengths of the UV light into the target zone. For example, the one or more UV light emitters 108 may be mounted within a housing of the UV lamp 104, and the wavelength selective filter 110 may be attached to the housing extending across a path of the UV light that is emitted from the one or more UV light emitters 108. The wavelength selective filter 110 may be utilized as a bandpass filter (which absorbs or blocks light at wavelengths both above and below a transmission region, referred to as a bandpass region), a bandstop filter (which only absorbs or blocks light at wavelengths within a designated bandstop region), a shortpass filter (which only absorbs or blocks light at wavelengths above the transmission region), or a longpass filter (which only absorbs or blocks light at wavelengths below the transmission region). The term transmission region broadly refers to the range of wavelengths of light permitted to pass through the wavelength selective filter according to the embodiments described herein. In one or more embodiments, the wavelength selective filter 110 may be designed as a bandpass filter that only allows transmission of a narrow range of UV wavelengths into the target zone. The narrow wavelength range that is permitted to pass through the filter may be within the far UV and/or UV-C spectrum, such as a narrow range disposed between the bookends of 200 nm and 280 nm. The narrow wavelength range may have a width of less than 20 nm, such as less than 10 nm or even less than 6 nm. The narrow wavelength range may be centered around a designated wavelength, such as 222 nm.

The UV lamps 104 include a power supply 112 that provides electrical energy to the one or more UV light emitters 108 to generate the UV light. The power supply 112 may include a power cord for connecting to an external power source. Optionally, the power supply 112 may include an electrical energy storage device, such as a battery pack, capacitors, and/or the like. The power supply 112 may include only one of the power cord or the energy storage device, or may have both components. The power supply 112 may include or be connected with control circuitry and/or switching devices that can be controlled by the control unit 106 to activate, deactivate, and/or dynamically modulate the power supplied to the UV light emitters 108 according to the operations and algorithms described herein. The power supply 112 is shown integrated with the UV lamp 104 in FIG. 1, but optionally the power supply 112 may be remote from the one or more UV lamps 104. For example, the power supply 112 may be a discrete and separate device that is electrically connected to one or more UV lamps 104 via respective electrically conductive leads, such that the power supply 112 distributes electrical energy to the UV lamps 104 to power the UV light generation.

The sanitizing system 100 includes one or more occupancy sensors 102 that monitor corresponding zones within the space. Sensor signals generated by the occupancy sensors 102 are analyzed to determine an occupancy status of at least a target zone within the space, as described herein.

Each occupancy sensor 102 is configured to monitor a corresponding region of the space and generate sensor signals over time that can be analyzed to determine an occupancy of the region. The occupancy sensors 102 may use various working mechanisms to detect when one or more persons are present in the space. In one or more embodiments, the occupancy sensors 102 monitor temperature. The sanitizing system 100 in an embodiment includes an infrared (IR) sensor that generates thermal image data.

The sanitizing system 100 may include only one IR sensor, or may have at least two IR sensors. Optionally, at least one other type of occupancy sensor 102 may be utilized by the sanitizing system 100 monitor temperature, such as a thermocouple, thermistor, or the like. In an embodiment, the sanitizing system 100 includes a first occupancy sensor that is an IR sensor, and a second occupancy sensor that is either another IR sensor, a thermocouple, or a thermistor. Optionally, the sanitizing system 100 may include additional types of occupancy sensors 102 that do not measure temperature, such as pressure sensors, photoelectric sensors, cameras that generate image data in the visible wavelength spectrum, acoustic sensors, optical sensors, or contact sensors. The occupancy sensors 102 may generate sensor signals at fixed intervals or in response to detecting a changed condition in the space, and communicate the sensor signals to the control unit 106.

The control unit 106 is communicatively connected to the one or more UV lamps 104 and the one or more occupancy sensors 102 via wired and/or wireless communication pathways. The control unit 106 generates control signals that control the operation of the UV lamps 104. The control signals may control the operation of the UV lamp 104 by controlling the presence and characteristics of electrical energy (e.g., voltage, current, phase, etc.) that is supplied to the UV light emitters 108. For example, the control unit 106 can selectively activate the UV lamps 104 to cause the UV light emitters 108 to emit UV light. The control unit 106 can selectively deactivate the UV lamps 104 to block or stop the UV light emitters 108 from emitting UV light. The UV lamps 104 are in an active state when emitting UV light, and are in an inactive state when not emitting UV light. The control unit 106 may also modify, adjust, modulate, or vary the output levels of the UV light emitted by the UV lamps 104 by controlling characteristics of the electrical energy supplied to the UV lamps 104, such as voltage, frequency, pulse width, and the like. The control unit 106 may generate at least some of the control signals to control the one or more UV lamps 104 based on sensor signals generated by the one or more occupancy sensors 102. More specifically, according to one or more embodiments, the control unit 106 selectively controls the operation of the UV lamps 104 over time based on IR thermal image data generated by an IR sensor of the one or more occupancy sensors 102.

The control unit 106 represents hardware circuitry that includes and/or is connected with one or more processors 114 (e.g., one or more microprocessors, integrated circuits, microcontrollers, field programmable gate arrays, etc.). The control unit 106 includes and/or is connected with a tangible and non-transitory computer-readable storage medium (e.g., memory) 116. For example, the memory 116 may store programmed instructions (e.g., software) that is executed by the one or more processors 114 to perform the operations of the control unit 106 described herein.

Figure 2:
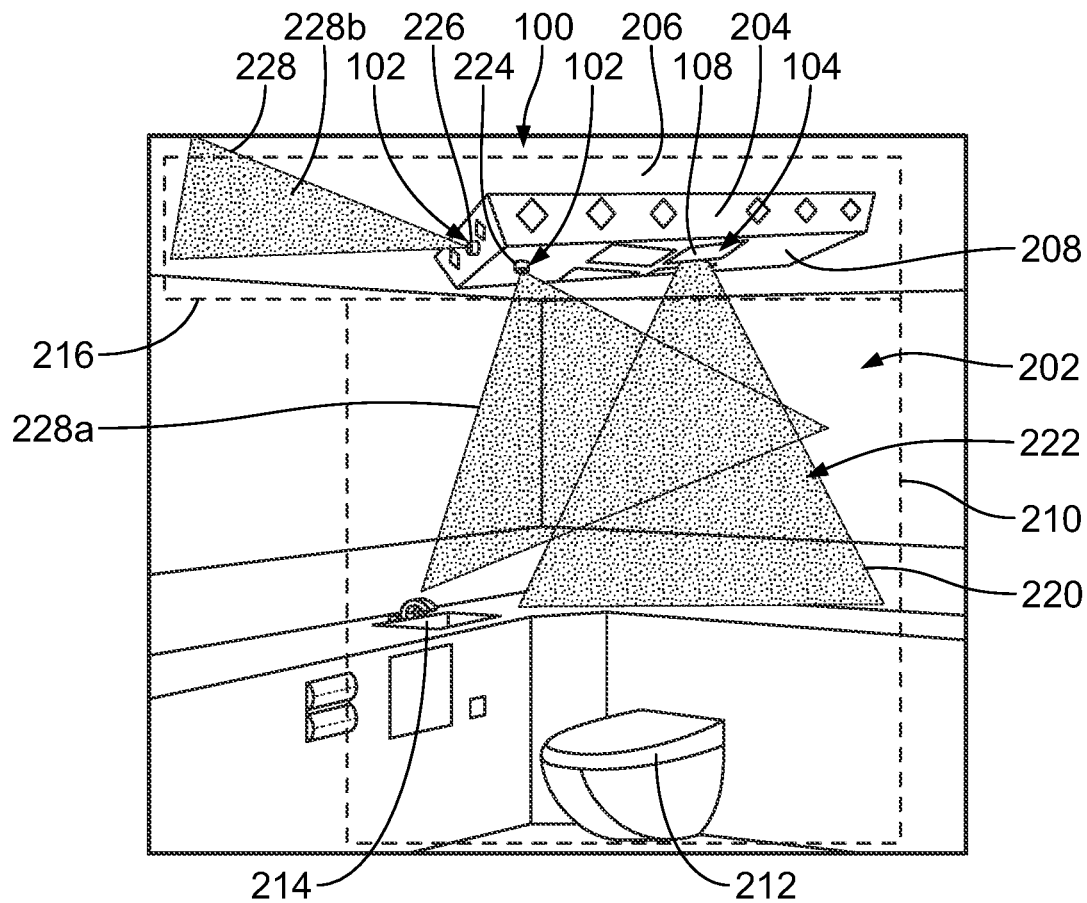
FIG. 2 illustrates a perspective internal view of the sanitizing system within a space, according to an embodiment of the present disclosure.

FIG. 2 illustrates a perspective internal view of the sanitizing system 100 within a space 202, according to an embodiment of the present disclosure. In the illustrated embodiment, at least some of the components of the sanitizing system 100 are installed within an enclosure 204 or housing. The enclosure 204 is mounted to a ceiling 206 of the space 202 in the illustrated embodiment. Optionally, the enclosure 204 may be integrated into the ceiling 206 such that the enclosure 204 is flush with the ceiling 206 instead of suspended from the ceiling 206. In FIG. 2, the space 202 is illustrated as a lavatory, such that the ceiling 206 is a portion of the lavatory. However, other spaces are possible as well. For instance, in one or more embodiments, the sanitizing system 100 may monitor and emit UV light into a space 202 that can be any space in or around a vehicle, building, structure, facility, or the like. Further, the space 202 may be an enclosed area or room, but need not be enclosed.

The sanitizing system 100 in FIG. 2 includes a UV lamp 104 and two occupancy sensors 102. The UV lamp 104 may include one UV emitter 108 or multiple UV emitters 108. The UV lamp 104 is disposed along a bottom panel 208 of the enclosure 204, and the UV emitters 108 face downward to emit UV light towards one or more components within a target zone 210 of the space 202. The UV lamps 104 emits UV light within a field of illumination 220 of the UV lamp 104, defining an illumination zone 222.

The UV lamp 104 may be positioned (e.g., located and oriented) within the space 202 to direct the UV light towards one or more specific components within the target zone 210. The components that receive UV light may have surfaces that receive frequent contact from people that access the space 202. In the illustrated embodiment, the components in the target zone 210 that are illuminated by the UV light may include a toilet 212, a sink and surrounding countertop 214, and a door of the space 202. The target zone 210 represents a portion or region of the space that may be at least occasionally occupied and utilized by people. For example, the target zone 210 may represent the space within the space 202 that a person may access and occupy during ordinary use of the space 202. For example, the target zone 210 in FIG. 2 encompasses the toilet 212, the countertop 214, the door, and the intervening spaces. The target zone 210 may not encompass the enclosure 204 if the enclosure 204 is located sufficiently high above the floor of the space 202 that most people would not access unless standing on a step ladder or other structure, which is not ordinary use of the space 202. The region or regions of the space 202 outside of the target zone 210 may be referred to as non-target zone(s) 216. The non-target zone 216 shown in FIG. 2 is located adjacent the target zone 210. For example, the non-target zone 216 is above the target zone 210, and encompasses the enclosure 204. The non-target zone 216 is predetermined or designated as an unoccupied zone because the non-target zone 216 is not expected to be occupied. A temperature of the non-target zone 216, such as the temperature of the air or a component within the non-target zone 216, can be used to represent a reference temperature for occupancy detection, as described herein. The reference temperature may represent an ambient temperature of the space.

Although only one UV lamp 104 is shown in FIG. 2, the sanitizing system 100 may include multiple UV lamps 104 that emit UV light into the target zone 210. The UV lamps 104 may be positioned to emit UV light towards different components. For example, one UV lamp 104 may emit UV light towards the toilet 212 or at least a part of the toilet 212, such as toilet seat lid and/or a flush actuator. A second UV lamp 104 may emit UV light towards the sink and countertop 214. A third UV lamp 104 may emit UV light towards the door used to enter and exit the space 202, particularly towards high-touch areas of the door, such as a handle, a push plate, and/or a latching mechanism for locking the door. Optionally, two or more UV lamps 104 may be positioned to emit UV light towards a common target component, such that the fields of illumination of the two or more UV lamps 104 overlap. The components within an overlap region may experience enhanced disinfection due to a reduction in shadows and an increased irradiance of UV energy received. When multiple UV lamps 104 are used, the UV lamps 104 may be spaced apart from each other, such as located at different ends of the enclosure 204 or even mounted to structures in the space 202 remote from the enclosure 204. In an alternative embodiment, multiple UV lamps 104 may be physically adjacent, although may be oriented differently to emit UV light in different directions from one another.

As mentioned above, sanitizing system 100 includes one or more occupancy sensors 102. In the illustrated example of FIG. 2, the one or more occupancy sensors 102 include a first sensor 224 and a second sensor 226. The first sensor 224 is an IR sensor, and is referred to herein as IR sensor 224 and first IR sensor 224. In the illustrated embodiment, the second sensor 226 is also an IR sensor, and is referred to herein as second IR sensor 226. Each of the IR sensors 224, 226 is configured to use IR signals to monitor (e.g., measure) the temperature of the environment within a respective field of view 228. The field of view 228a of the first IR sensor 224 is directed into the target zone 210 to monitor temperature within the target zone 210. The field of view 228b of the second IR sensor 226 is directed into the non-target zone 216 to monitor temperature within the non-target zone 216. For example, both the IR sensors 224 may generate respective thermal image data that is associated with the components located within the respective field of view 228. The thermal image data generated by the first IR sensor 224 may represent thermal properties of components (e.g., objects and structures) within the field of view 228a, and the thermal image data generated by the second IR sensor 226 may represent thermal properties of components within the field of view 228b.

Figure 3:
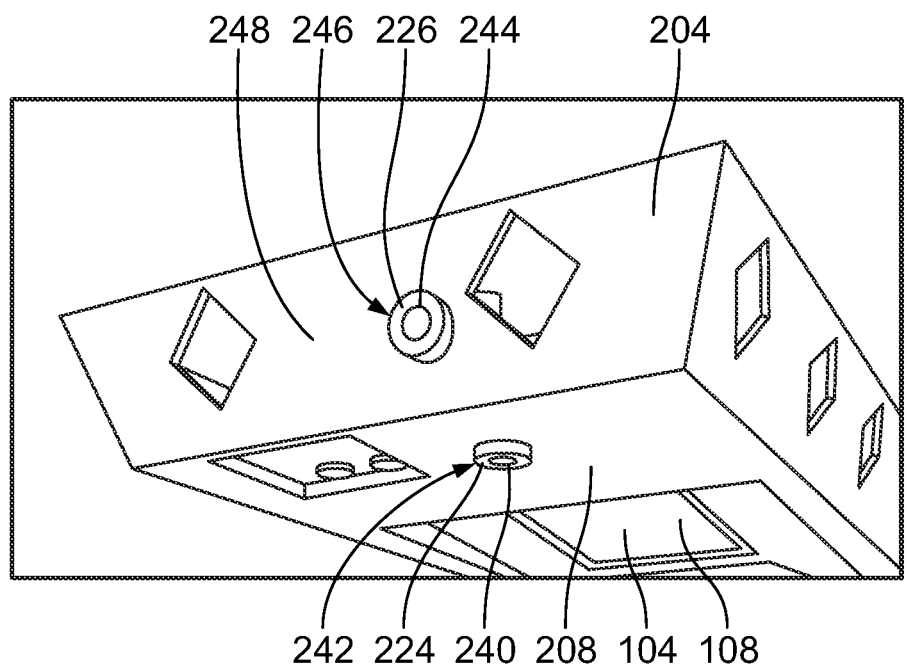
FIG. 3 illustrates an end view of an enclosure of the sanitizing system, according to an embodiment of the present disclosure.

Reference is now made to FIG. 3, which illustrates an end view of the enclosure 204 of the sanitizing system 100 according to an embodiment. In the illustrated embodiment, the first and second IR sensors 224, 226 are held by the enclosure 204, as with the UV lamp 104. For example, the first IR sensor 224 is primarily disposed within the enclosure 204, and an end 240 of the IR sensor 224 aligns with an opening 242 through the bottom panel 208 of the enclosure 204. Optionally, the end 240 may protrude through the opening 242 to provide a clear view of the target zone 210 below the enclosure 204. The second IR sensor 226 is primarily disposed within the enclosure 204, and an end 244 of the IR sensor 226 aligns with an opening 246 through a side panel 248 of the enclosure 204. The end 244 may protrude through the opening 246. The opening 246 for the second IR sensor 226 may be located along the side panel 248 to enable the second IR sensor 226 to monitor the non-target zone 216 shown in FIG. 2.

The enclosure 204 may have a box-like shape to conceal most of the components of the sanitizing system 100. For example, in addition to the UV lamp 104 and the IR sensors 224, 226, the hardware circuitry of the control unit 106 (shown in FIG. 1) may be disposed within the enclosure 204. The enclosure 204 may have a relatively thin, low-profile shape to limit the footprint within the space 202.

In an alternative embodiment, the sanitizing system 100 does not include the enclosure 204. For example, the UV lamp (or lamps) 104 and the IR sensors 224, 226 may be mounted directly to walls, ceilings, cabinets, mirrors, doors, and/or the like, without being positioned within a common enclosure. The control unit 106 may be integrated with one of the UV lamps 104 or IR sensors 224, 226, or alternatively may be a discrete device that is separately mounted. For example, the control unit device may be mounted outside of the space 202 or within the space 202. Inside the space 202, the control unit device could be stowed behind a wall, the ceiling, or the floor, or may be mounted in, to, or behind a structure, such as a vanity. One or more wires or wireless pathways may extend from the control unit 106 to the UV lamp 104 and the IR sensors 224, 226 to establish communication between the components of the sanitizing system 100.

Figure 4:
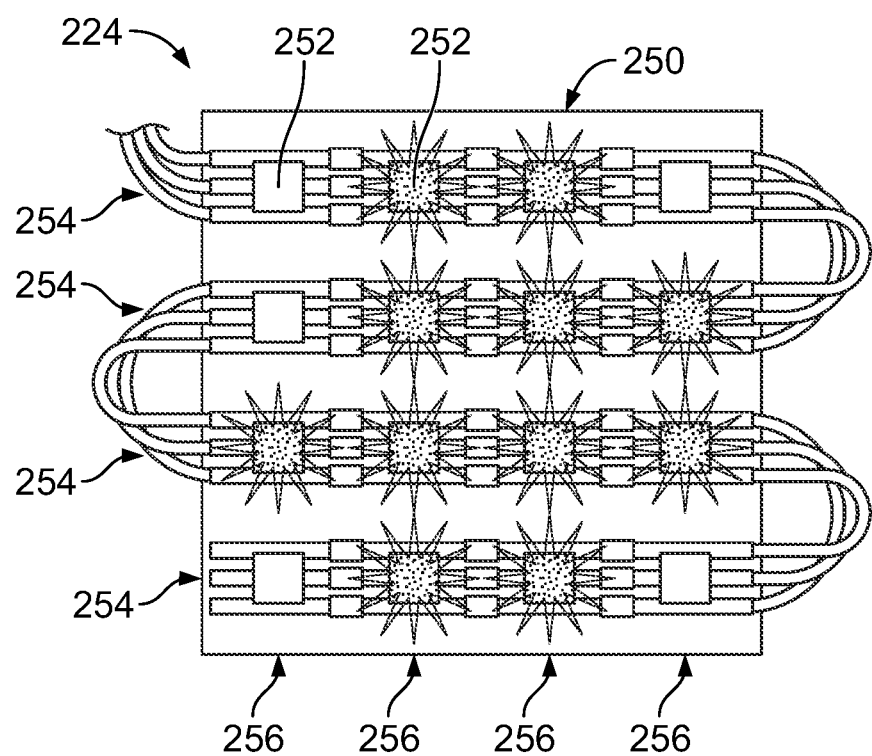
FIG. 4 illustrates an exposed view of an IR sensor of the sanitizing system, according to an embodiment of the present disclosure.

FIG. 4 illustrates an exposed view of the IR sensor 224 according to an embodiment. The IR sensor 224 includes an array 250 of pixels 252. The pixels 252 in the array 250 are arranged in a grid of rows 254 and columns 256. In the illustrated embodiment, the IR sensor 224 has 16 pixels 252 in a 4×4 array 250. The IR sensor 224 optionally may have more or less than 16 pixels 252 in another embodiment. In a non-limiting example, the IR sensor 224 may be an Omron D6T MEMS thermal sensor. The pixels 252 are positioned to monitor different areas of the target zone 210 relative to one another, and generate different portions of the thermal image data corresponding to the different monitored areas of the target zone 210. Optionally, the second IR sensor 226 shown in FIG. 2 may be the same type of thermal sensor as the IR sensor 224 shown in FIG. 4.

Referring now back to FIGS. 1 and 2, the control unit 106 of the sanitizing system 100 determines an occupancy status of the target zone 210 based on thermal image data generated by the first IR sensor 224 and a reference temperature of the space. The occupancy determination described herein is beneficial, at least in part, because it is not dependent on motion or a changing environment. The sanitizing system 100 can detect the presence of stationary people, such as sleeping individuals, even after an extended period of time without movement. Other non-moving occupants are possible as well. For instance, in an example, the non-moving occupant can be a stationary seated individual or a stationary standing individual. The sanitizing system 100 may operate based on absolute temperature, not motion, so there is negligible risk of the sanitizing system 100 normalizing to a static, occupied environment and registering a false unoccupied status.

The thermal image data generated by the first IR sensor 224 indicates an absolute temperature of one or more components (e.g., objects, structures, and the like) disposed within the target zone 210. For example, the IR sensor 224 may be calibrated for the thermal image data to provide absolute temperature. The thermal image data may provide a map of multiple absolute temperature values corresponding to different monitored areas within the field of view 228a of the IR sensor 224.

The control unit 106 receives the thermal image data that is generated by the IR sensor 224. The control unit 106 also receives the reference temperature for the space. The reference temperature may be an ambient temperature of the space. In the illustrated embodiment, the reference temperature is determined based on thermal image data generated by the second IR sensor 226. For example, the second IR sensor 226 generates thermal image data associated with the non-target zone 216. As described above, the non-target zone 216 may be proximate to the target zone 210 such that the non-target zone 216 has a similar ambient temperature profile as the target zone 210. In FIG. 2, the non-target zone 216 is adjacent the target zone 210 and located above the target zone 210. The non-target zone 216 is predetermined as being unoccupied, so the thermal image data generated by the second IR sensor 226 is not expected to be associated with the temperature of a person.

In an alternative embodiment, the second sensor 226 is not an IR sensor. Rather, the second sensor 226 may be a conventional resistive-based temperature sensor, such as a thermocouple or thermistor. The second sensor 226 is located in the non-target zone 216 and generates sensor data that indicates a measured temperature within the non-target zone 216. The control unit 106 receives the sensor data and utilizes the measured temperature as the reference temperature.

The control unit 106 is configured to determine a threshold temperature based on the reference temperature. Then, the control unit 106 compares the absolute temperature in the target zone 210, as indicated by (or based on) the thermal image data of the IR sensor 224, to the threshold temperature to determine the occupancy status. In an embodiment, if the absolute temperature in the target zone 210 is greater than the threshold temperature, the control unit 106 determines that the target zone 210 is occupied (e.g., the occupancy status is occupied). Detecting an absolute temperature above the threshold indicates that at least one person is present in the target zone 210. For example, the temperature of the person's skin, measured in the thermal image data, exceeds the threshold temperature. If the absolute temperature within the target zone 210 is less than or equal to the threshold temperature, the control unit 106 determines the occupancy status of the target zone 210 as unoccupied. The unoccupied status indicates that no people are present in the target zone 210 at the time.

In an embodiment, the threshold temperature is dependent on the reference temperature. In an example, the control unit 106 selects the threshold temperature based on the reference temperature. In an example, the control unit 106 varies or modulates the threshold temperature in response to a detected change in the reference temperature. The threshold temperature is adjusted to ensure accuracy of the occupancy detection process. For example, as described above, a threshold temperature of 80° F. works well in an environment that is about 70° F., because the temperature of a living person's skin in that environment would be above 80° F. while most inanimate objects would be below 80° F. However, if the ambient temperature increases to about 80° F. or above, eventually the temperature of some inanimate objects may exceed the threshold temperature, incorrectly triggering an occupied status. Furthermore, if the ambient temperature dropped considerably, the temperature of a person's skin may fall below the 80° F. threshold temperature, incorrectly triggering an unoccupied status. The threshold temperature is adjusted based on the reference temperature to reduce or eliminate the possibility of incorrect occupancy statuses. For example, the control unit 106 may lower the temperature threshold in response to a drop in the reference temperature. The control unit 106 may increase the temperature threshold in response to a rise in the reference temperature.

The correlation between the measured reference temperature and the threshold temperature may be based on predictive modeling using an artificial intelligence agent or a learned calibration based on historical and/or experimental data. The correlation may consider the relationship that ambient temperature has on the measured temperature of a person's skin. In an embodiment, once the correlation is determined, the correlation may be characterized in a function (e.g., equation or model), a look-up table, or the like.

Figure 5:
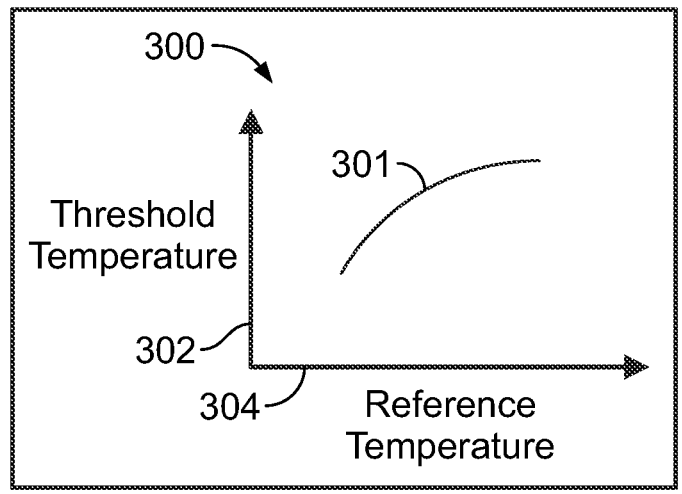
FIG. 5 is a graph depicting threshold temperature as a function of reference temperature, according to an embodiment of the present disclosure.

FIG. 5 is a graph 300 depicting threshold temperature as a function of reference temperature according to an embodiment. The vertical axis 302 represents threshold temperature, and the horizontal axis 304 represents reference temperature. The illustrated trendline 301 represents the function. The function may be stored in the memory 116 of the control unit 106. For example, once the control unit 106 determines the reference temperature based on the sensor data generated by the second sensor 226, the control unit 106 (or the processors 114 thereof) may input the reference temperature into the function to calculate the threshold temperature. In a non-limiting example, if the reference temperature is 40° F., the threshold temperature may be 60° F. based on the function. A reference temperature of 70° F. may yield a threshold temperature of 85° F., and a reference temperature of 85° F. may produce a threshold temperature of 92° F. Optionally, as shown in FIG. 5, the function may not be a linear relationship. Alternatively, the correlation or relationship may be stored in the memory 116 in the form of a look-up table or database that contains a list of threshold temperatures and reference temperatures in matched pairs instead of a mathematical function or equation.

The reference temperatures are typically below the absolute temperature of a person, so the threshold temperature is generally a variable value that is between the reference temperature and the temperature of a person. The differential between the threshold temperature and the reference temperature may decrease as the reference temperature increases. This logic can also be extended to reference temperatures that are above the absolute temperature of a person's skin. In this case, the threshold temperature may be below the reference temperature, and occupancy may be detected if the absolute temperature is below the threshold temperature. However, occupied spaces in vehicles and buildings that utilize occupancy detection for UV sanitizing are not typically at or above 100° F.

In an embodiment, a function for calculating the threshold temperature based on the reference temperature is $T_{thr}=T_{ref}+X$. When $T_{ref}<60°$ F., $X=13°$ F. When $T_{ref}>94°$ F., $X=-3°$ F. When $60 \leq T_{ref} \leq 94°$ F., $$X = 20\left(\frac{85}{(Tref - 10)} - 1\right).$$

In this formula, X is a variable that is a function of the reference temperature. Any measured temperature that is above the temperature threshold ($T_{thr}$) is an indication of occupancy.

As described with reference to FIG. 4, the IR sensor 224 in an embodiment has an array 250 of pixels 252 positioned to monitor different areas of the target zone 210 relative to one another, and generate different portions of the thermal image data corresponding to the different monitored areas of the target zone 210. Stated differently, each of the pixels 252 may generate the absolute temperature of a different point or area in the target zone 210. For example, the field of view 228a of the IR sensor 224 may be essentially an aggregate of individual fields of view of the different pixels 252 in the array 250. Each of the sixteen pixels 252 may represent a one-sixteenth sliver of the field of view 228a and may generate approximately one-sixteenth of the thermal image data shown.

In the illustrated embodiment in FIG. 2 in which the second sensor 226 is an IR sensor, the reference temperature may be determined as an average value of each of the pixels of the second IR sensor 226 are known to monitor the non-target zone 216. For example, if all pixels of the IR sensor 226 are directed to the non-target zone 216, then the reference temperature may be an average of the absolute temperature generated by each of the pixels. If a given pixel is directed into the target zone 210, then that absolute temperature data from the given pixel directed into the target zone 210 is not used to measure the reference temperature.

The control unit 106 may apply the occupancy logic to the absolute temperature data generated by each of the pixels 252 of the first IR sensor 224 to determine the occupancy status of the target zone 210. The control unit 106 may determine individual occupancy statuses for different monitored areas within the target zone 210 by comparing the absolute temperature associated with the corresponding monitored area to the threshold temperature. For example, the control unit 106 may determine an individual occupancy status for a first area of the target zone 210 by comparing the absolute temperature generated by a first pixel 252, pointed to the first area, to the threshold temperature. The control unit 106 may determine the individual occupancy status for a second area of the target zone 210 by comparing the absolute temperature generated by a second pixel 252, pointed to the second area, to the threshold temperature. The control unit 106 may aggregate the individual occupancy statuses to make a final determination about the occupancy status of the target zone 210. For example, if any of the individual occupancy statuses indicate that the corresponding monitored area of the target zone is occupied, the control unit 106 determines that the target zone 210 is occupied. In an example, the control unit 106 determines that the target zone is unoccupied only when none of the individual occupancy statuses indicates that the corresponding monitored area of the target zone 210 is occupied.

Figure 6:
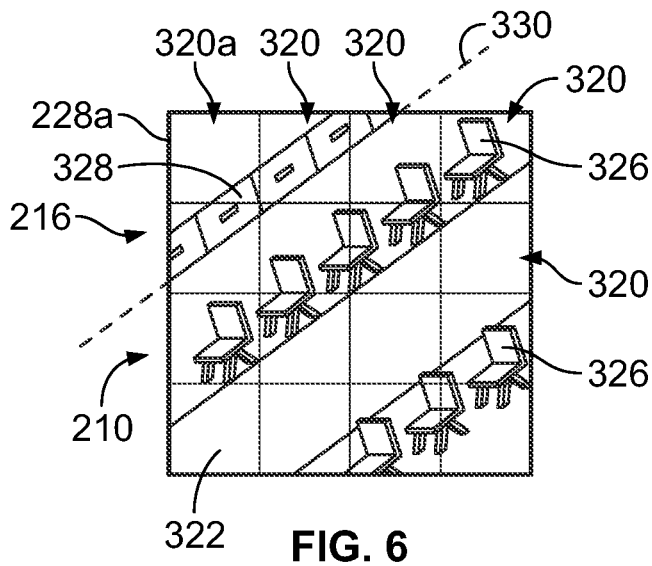
FIG. 6 illustrates a field of view of the IR sensor, according to an embodiment of the present disclosure.

FIG. 6 illustrates the field of view 228a of the IR sensor 224 according to an embodiment. The field of view 228a is segmented into a grid of sixteen boxes which represent the areas 320 monitored by each of the individual pixels 252. For example, each of the areas 320 is monitored by a different pixel 252 of the IR sensor 224. The field of view 228a in FIG. 6 encompasses various components within an internal cabin, including an aisle 322, two lines or columns 324 of passenger seats 326 on either side of the aisle 322, and passenger stowage compartments or bins 328.

In an embodiment, the IR sensor 224 may be fixed in place, such that the components within the field of view 228a generally remain consistent over multiple periods of time although additional objects, such as people, may intermittently occupy the field of view 228a. The period of time may include days, weeks, and/or months. In an embodiment, the control unit 106 may determine a respective baseline temperature profile for each of the monitored areas 320 based on thermal image data generated by the associated pixels 252 over time. For example, the baseline temperature profiles can be used to determine relative temperature differences between different monitored areas 320. The control unit 106 may use the baseline temperature profiles during the occupancy determination. In one example scenario, the baseline temperature profiles can be used to ignore absolute temperature data (e.g., thermal image data) that is determined to be irrelevant to the occupancy determination. For example, one of the monitored areas 320 encompasses a coffee maker, a heater, or some other actively powered device that causes the absolute temperature data generated by the associated pixel 252 to consistently be relatively high, such as above the threshold temperature. The control unit 106 may determine, based on either the magnitude of the measured absolute temperature or the consistency, that the heat is not the product of at least one person in the monitored area, and may disregard additional data generated by that pixel 252. The baseline temperature profiles optionally may be used to modulate, at least slightly, the threshold temperature. For example, the threshold temperature may be individually adjusted, at least slightly, for each pixel based on the respective baseline temperature profile, which may account for slight temperature gradients between pixels 252.

In an alternative embodiment, the sanitizing system 100 may not include the second sensor 226 shown in FIG. 2. In such an alternative embodiment, both the absolute temperature and the reference temperature may be determined using the thermal image data of the IR sensor 224. For example, the IR sensor 224 may be positioned and oriented relative to the space such that the field of view 228a encompasses at least a portion of both the target zone 210 and the non-target zone 216. The control unit 106 may know which portion of the thermal image data generated by the IR sensor 224 corresponds to the target zone 210 and which portion corresponds to the non-target zone 216. Based on this knowledge, the control unit 106 can utilize the thermal image data calibrated to absolute temperature of the non-target zone 216 as the reference temperature. The reference temperature is then used to determine the threshold temperature. The portion of the thermal image data that is associated with the target zone 210 is used by the control unit 106 to determine the one or more absolute temperatures that are compared to the threshold temperature to determine the occupancy status of the target zone 210.

In an example in which the IR sensor 224 includes multiple pixels 252 in the array 250, such as the IR sensor illustrated in FIG. 4, a first subset of the pixels 252 (e.g., one or more of the pixels 252) may be directed to the target zone 210, and a second subset of the pixels 252 (e.g., one or more of the pixels 252) may be directed to the non-target zone 216. In an example, the first subset includes one or more pixels 252 in a corner of the IR sensor 224, and the second subset include the remaining pixels 252 of the IR sensor. In an example, with reference to FIG. 6, the target zone 210 may be defined as the space below the stowage bins 328, and the non-target zone 216 is the space aligned with and above the stowage bins 328. The line 330 defines the border between the two zones 210, 216. The monitored area 320a corresponding to one of the pixels 252 is entirely (or almost entirely) within the non-target zone 216. The control unit 106 may segregate the thermal image data generated by the pixel 252 that monitors the area 320a from the other thermal image data, and may use the thermal image data from that pixel 252 to determine the reference temperature. The other monitored areas 320 in FIG. 6 may be within the target zone 210. Optionally, more than one pixel 252 may define the subset that is directed to the non-target zone 216.

In one or more embodiments, the control unit 106 operates the one or more UV lamps 104 of the sanitizing system 100 based on the determined occupancy status of the target zone 210. For example, in response to an occupied status while the one or more UV lamps 104 are active (e.g., emitting UV light), the control unit 106 may either deactivate the UV lamps 104 to stop further UV light emission into the space, or may reduce an output level of the one or more UV lamps 104. The control unit 106 may control the UV lamps 104 by generating control signals that are communicated to circuitry, such as switch devices, within the UV lamps 104 and/or an external power supply device. Optionally, the control unit 106 may initially reduce the output level (e.g., irradiance or intensity) of the UV light that is emitted, and then deactivate the UV lamps 104 if the occupation extends for longer than a predetermined period of time.

In an embodiment, in response to the occupancy status indicating that the target zone is unoccupied, the control unit 106 may operate the UV lamp 104 (or lamps) to emit UV light at a full irradiance level to disinfect one or more components. The full irradiance level may represent a full power setting or high power setting that is used to disinfect the components in the space when the space is unoccupied. If the space remains unoccupied, the control unit 106 may eventually deactivate the UV lamp 104 to cease emitting UV light at the full irradiance level after a predetermined time period for disinfection has elapsed. For example, deactivating the UV lamp 104 after the designated time period conserves energy. The designated time period represent the duration of a disinfection cycle, and may be on the order of minutes, such as 1 minute, 5 minutes, 10 minutes, 20 minutes, or the like. The designated time period for disinfection may be selected based on the irradiance of the UV light, the distance of the UV lamp 104 from the one or more components, and a desired dose of UV light to be applied to the one or more components. For example, the UV dose depends on the irradiance of the UV light, the proximity of the UV light, and the duration at which the UV light irradiates the one or more components, so the duration may be selected in order to achieve the desired dose without expending additional energy. As an example, the designated time period may be longer for a UV lamp that has a lower irradiance and/or is located farther from the target components being disinfected in order to provide a predetermined dose of UV light to the target components.

When the one or more UV lamps 104 are inactive (e.g., not emitting UV light), the control unit 106 be programmed to maintain the UV lamps 104 as inactive (e.g., not activate the UV lamps 104) until after the target zone 210 is determined to be unoccupied. For example, prior to activating the UV lamps 104 for a duty cycle, the control unit 106 may check the occupancy status of the target zone 210. If the target zone 210 is occupied, the control unit 106 postpones the duty cycle until at least the space is no longer occupied. Additional UV control aspects of the control unit 106 based on the occupancy status are described herein with reference to FIGS. 11 and 12.

Figure 7:
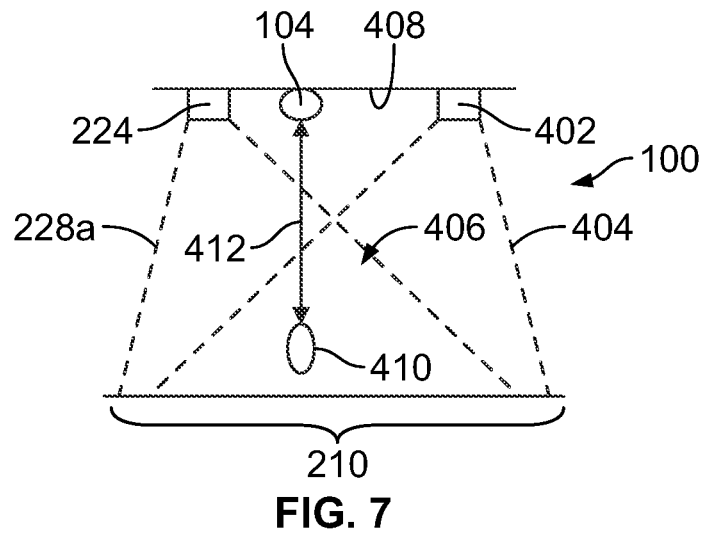
FIG. 7 illustrates a portion of the sanitizing system, according to another embodiment of the present disclosure.

FIG. 7 illustrates a portion of the sanitizing system 100 according to another embodiment. In FIG. 7, the sanitizing system 100 includes two IR sensors that generate thermal image data of the target zone 210. The two IR sensors include the first IR sensor 224 and a second IR sensor 402. The second IR sensor 402 is different from the second IR sensor 226 shown in FIG. 2 because the second IR sensor 226 is not directed to the target zone 210. In an example, the sanitizing system 100 in FIG. 7 also includes a third IR sensor that is positioned to monitor a temperature of the non-target zone 216, like the second IR sensor 226 in FIG. 2.

The second IR sensor 402 is spaced apart from the first IR sensor 224 and oriented such that a field of view 404 of the second IR sensor 402 overlaps the field of view 228a of the first IR sensor 224. For example, the individual fields of view of at least some pixels 252 of the first IR sensor 224 overlap with individual fields of view of at least some pixels of the second IR sensor 402. Both IR sensors 224, 402 are communicatively connected to the control unit 106. The control unit 106 is configured to analyze the thermal image data generated by the first IR sensor 224 and (second) thermal image data generated by the second IR sensor 402 to determine the occupancy status of the target zone 210. For example, overlapping the fields of view 228a, 404 may increase the accuracy of the occupancy determination, particularly with respect to determining occupancy within an area of the target zone 210 encompassed by an overlapping region 406 of the two fields of view 228a, 404.

Furthermore, due to the parallax effect, the control unit 106 may determine a location, within the space, of one or more components present in the overlapping region 406. The location may be a relative location that is relative to a wall or ceiling 408 on which the two IR sensors 224, 402 are mounted. In FIG. 7, an object 410 within the target zone 210 is encompassed by the overlapping region 406. Based on the thermal image data generated each by the two IR sensors 224, 402 corresponding to the overlapping region 406, the control unit 106 may use the parallax effect to determine a proximity of the object 410 to the IR sensors 224, 402 and/or to the wall or ceiling 408. The control unit 106 may use the location and/or proximity data to inform and/or confirm the occupancy determination. For example, if the object 410 is determined to have an absolute temperature above the threshold temperature, the location of the object can be checked against expected locations of people in the space, which could either increase or decrease the confidence of the determined occupancy status.

Furthermore, based on known locations of the IR sensors 224, 402 relative to a given UV lamp 104 that illuminates the object 410, the control unit 106 may determine a proximity 412 of the object 410 to the UV lamp 104. Based on the proximity 412, the control unit 106 may control operation of the UV lamp 104. For example, the control unit 106 may control the UV lamp 104 to generate a higher (or greater) output level of UV light if the object 410 is farther from the UV lamp 104 than if the object 410 is closer to the UV lamp 104. The control unit 106 may control the UV lamp 104 in increments based on the object 410 being within different predetermined proximity ranges of the UV lamp 104. For example, the UV lamp 104 may be controlled to provide a first UV output level in response to the object 410 being within a first proximity range of the UV lamp 104, and a second UV output level in response to the object 410 being within a second proximity range of the UV lamp 104. The second proximity range may be farther away from the UV lamp than the first proximity range, and the second UV output level may be higher than the first UV output level. By modulating or adjusting the UV light that is emitted based on proximity 412 of the object 410, the sanitizing system 100 can provide relatively consistent dosage of UV light to components in the target zone 210, without consuming excessive power to sanitize nearby components.

In one or more embodiments described herein, the sanitizing system 100 may monitor and emit UV light into a space that can be any space in or around a vehicle, building, structure, facility, or the like. The space may be an enclosed area or room, but need not be enclosed. In FIG. 2, the space 202 is a lavatory. In embodiments in which the sanitizing system 100 is installed within vehicles, the vehicles can be passenger vehicles such as buses, trains, aircraft, marine vessels, or the like. In a commercial aircraft, the sanitizing system 100 can be located within a cargo area, a flight deck, a lavatory, a galley, a rest area (e.g., crew rest and/or passenger rest), an assembly area, a lavatory waiting area, a passenger seating area (e.g., passenger cabin), a hallway, and other areas in which individuals, passengers, flight crew, ground crew, and/or maintenance personnel may occupy or enter). For example, the lavatory of FIG. 2 may be located within a vehicle, such as within the internal cabin of a commercial aircraft. Non-limiting examples of buildings or facilities in which the sanitizing system 100 can be installed include theatres, concert venues, arenas, places of worship, banquet halls, commercial businesses, factories, hospitals, and/or the like.

The lavatory in FIG. 2 is a room that defines a space 202, but the sanitizing system 100 is not limited to a single room. For example, the sanitizing system 100 may be present in any space, including a space that includes multiple rooms, hallways, and the like. Using the lavatory example shown in FIG. 2, the sanitizing system 100 may optionally include one or more UV lamps disposed outside of the space 202, such as in a galley, a passenger seating area, or the like. The control unit 106 may also control the operation of one or more UV lamps 104 disposed outside of the lavatory. The sanitizing system 100 may also include at least one occupancy sensor 102 disposed outside of the lavatory to detect occupancy of another target zone, such as a galley, passenger seating area, or the like. The sanitizing system 100 may be configured to sanitize a space 202 defined by an internal cabin of a vehicle, or alternatively may sanitize only a portion of the internal cabin, such as only the lavatory. Optionally, a vehicle may have multiple sanitizing systems 100 disposed at different locations within the internal cabin for sanitizing different portions and target components. For example, the sanitizing system 100 in the lavatory shown in FIG. 2 may represent a first sanitizing system, and a second sanitizing system (the same as or similar to the first sanitizing system 100) may be disposed within a passenger seating area.

Figure 8:
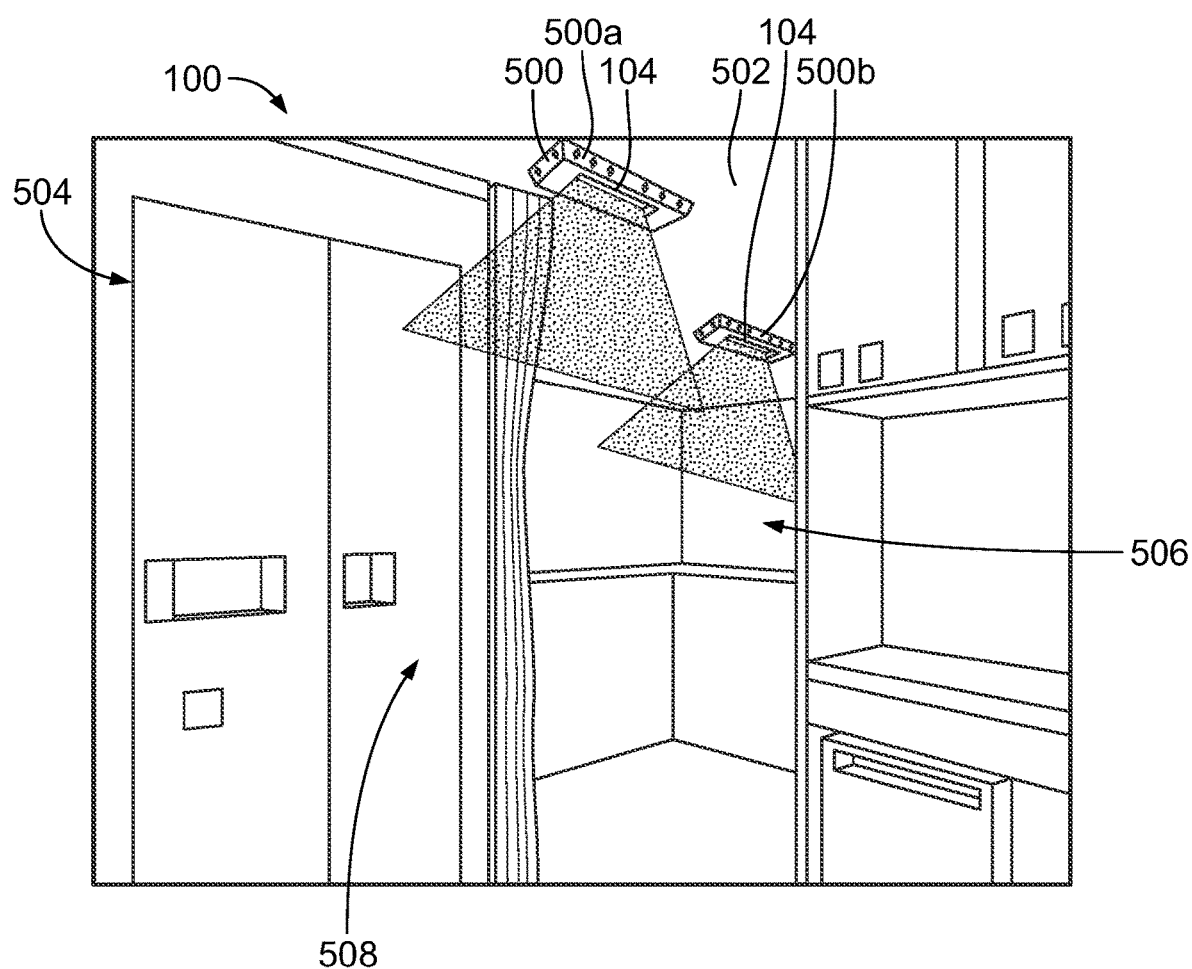
FIG. 8 illustrates the sanitizing system, according to an embodiment that includes multiple discrete UV lamp assemblies.

FIG. 8 illustrates the sanitizing system 100 according to an embodiment that includes multiple discrete UV lamp assemblies 500. The sanitizing system 100 includes a first UV lamp assembly 500a and a second UV lamp assembly 500b. The first UV lamp assembly 500a is mounted to a ceiling 502 within a first room or region of an internal cabin 504 of a vehicle. The second UV lamp assembly 500b is mounted to the ceiling 502 within a second room or region of the internal cabin 504. The first room or region may be a galley 506, and the second room or region may be a hallway and/or lavatory waiting area 508 adjacent to the galley 506. Each UV lamp assembly 500 includes at least one UV lamp 104 that emits UV light into a corresponding target zone to sanitize components within the target zone. The first UV lamp assembly 500a is spaced apart from the second UV lamp assembly 500b and has a different target zone than the second UV lamp assembly 500b.

Optionally, the two UV lamp assemblies 500a, 500b may represent two UV lamps 104 of a single sanitizing system 100. For example, both lamp assemblies 500a, 500b may be communicatively connected to and operated by the same control unit, which operates the UV lamp assemblies 500a, 500b based on the occupancy statuses of the galley 506 and the lavatory waiting area 508. Alternatively, the two UV lamp assemblies 500a, 500b may represent two discrete and independent sanitizing systems 100 that do not communicate with each other or share components.

Figure 9:
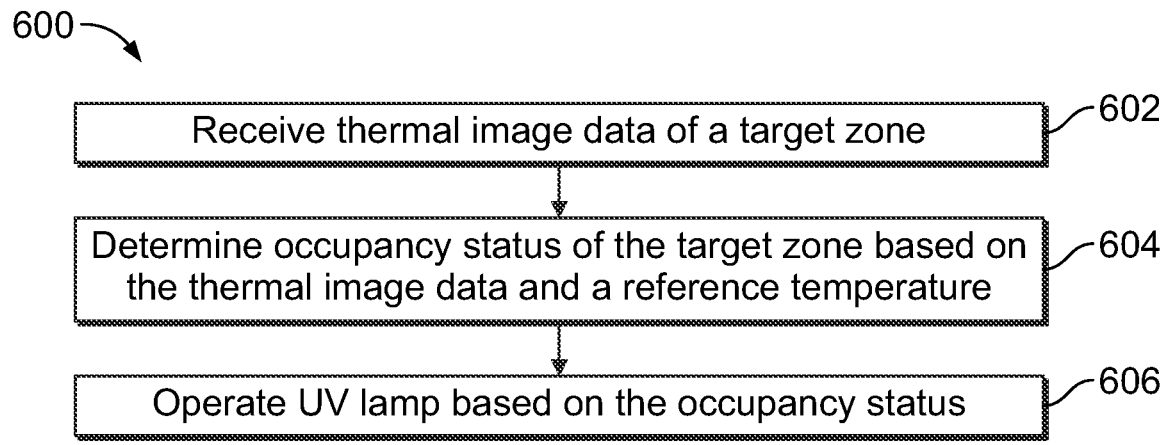
FIG. 9 illustrates a flow chart of a sanitizing method, according to an embodiment of the present disclosure.

FIG. 9 illustrates a flow chart 600 of a sanitizing method according to an embodiment of the present disclosure. Referring to FIGS. 1-9, the method begins at 602, at which thermal image data of a target zone 210 is received. The thermal image data is generated by the IR sensor 224. At 604, an occupancy status of the target zone 210 is determined, via the control unit 106, based on the thermal image data and a reference temperature.

At 606, one or more UV lamps 104 are operated, via the control unit 106, based on the occupancy status of the target zone 210. The one or more UV lamps 104 are operated to emit UV light into the target zone 210 to disinfect one or more components within the target zone 210. Optionally, when the one or more UV lamps 104 are active and the occupancy status indicates that the target zone 210 is occupied, the one or more UV lamps 104 are operated by (i) deactivating the UV lamps 104 to stop emitting the UV light or (ii) reducing an output level of the one or more UV lamps 104. Optionally, when the one or more UV lamps 104 are inactive, the one or more UV lamps 104 are operated by maintaining the one or more UV lamps 104 as inactive until after the occupancy status indicates that the target zone 210 is unoccupied.

Figure 10:
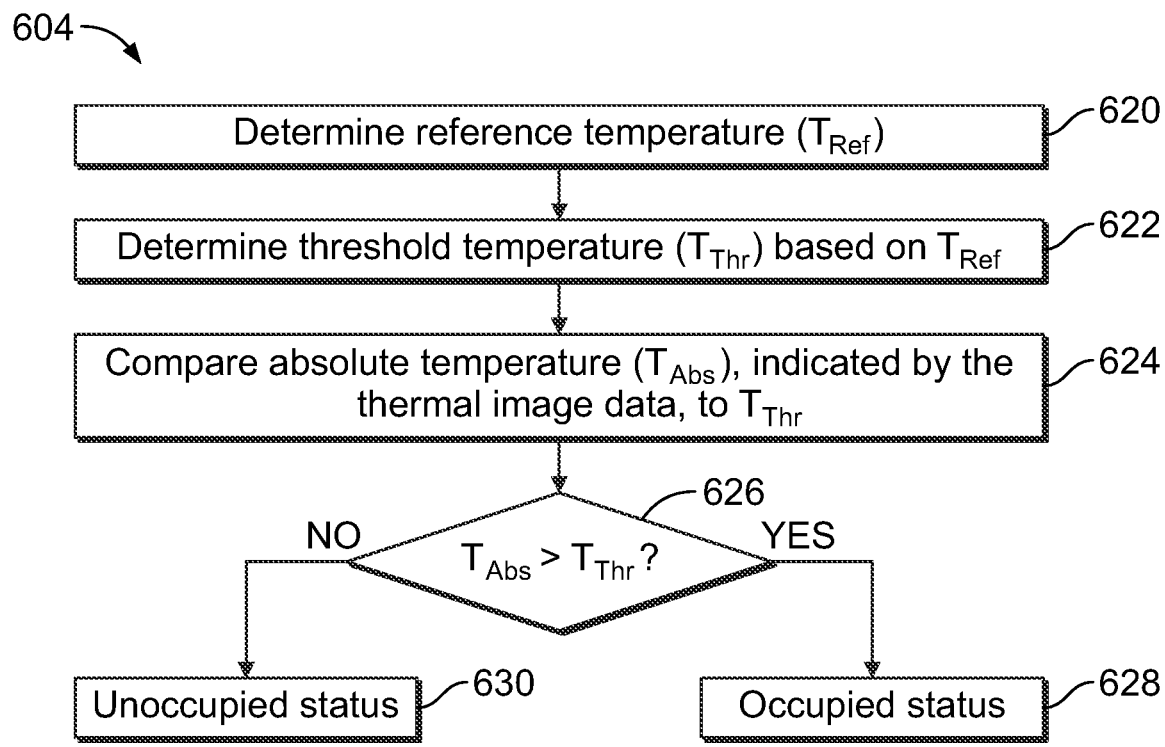
FIG. 10 is a flow chart of a method for determining an occupancy status of a target zone, according to an embodiment of the present disclosure.

FIG. 10 is a flow chart 604 of a method for determining an occupancy status of a target zone, according to an embodiment. The flow chart is labeled 604 to indicate that the method expounds step 604 of the flow chart 600 in FIG. 9. At 620, a reference temperature is determined. Optionally, the reference temperature may be determined based on second thermal image data generated by (i) the IR sensor 224 or (ii) a second IR sensor 226. The second thermal image data is associated with a non-target zone 216 that is designated as unoccupied.

At 622, a threshold temperature is determined based on the reference temperature. The threshold temperature may be a function of the reference temperature. The method may include modulating the threshold temperature based on a change in the reference temperature, such as increasing the threshold temperature based on a rise in the reference temperature and decreasing the threshold temperature based on a drop in the reference temperature.

At 624, an absolute temperature of the target zone 210 is compared to the threshold temperature. The absolute temperature is indicated by the thermal image data generated by the IR sensor 224. At 626, a determination is made whether the absolute temperature is greater than the threshold temperature. If the absolute temperature is indeed greater than the threshold temperature, the method proceeds to step 628 and the occupancy status is determined to be occupied. If, on the other hand, the absolute temperature is not greater than the threshold temperature, the method proceeds to step 630 and the occupancy status is determined to be unoccupied.

Figure 11:
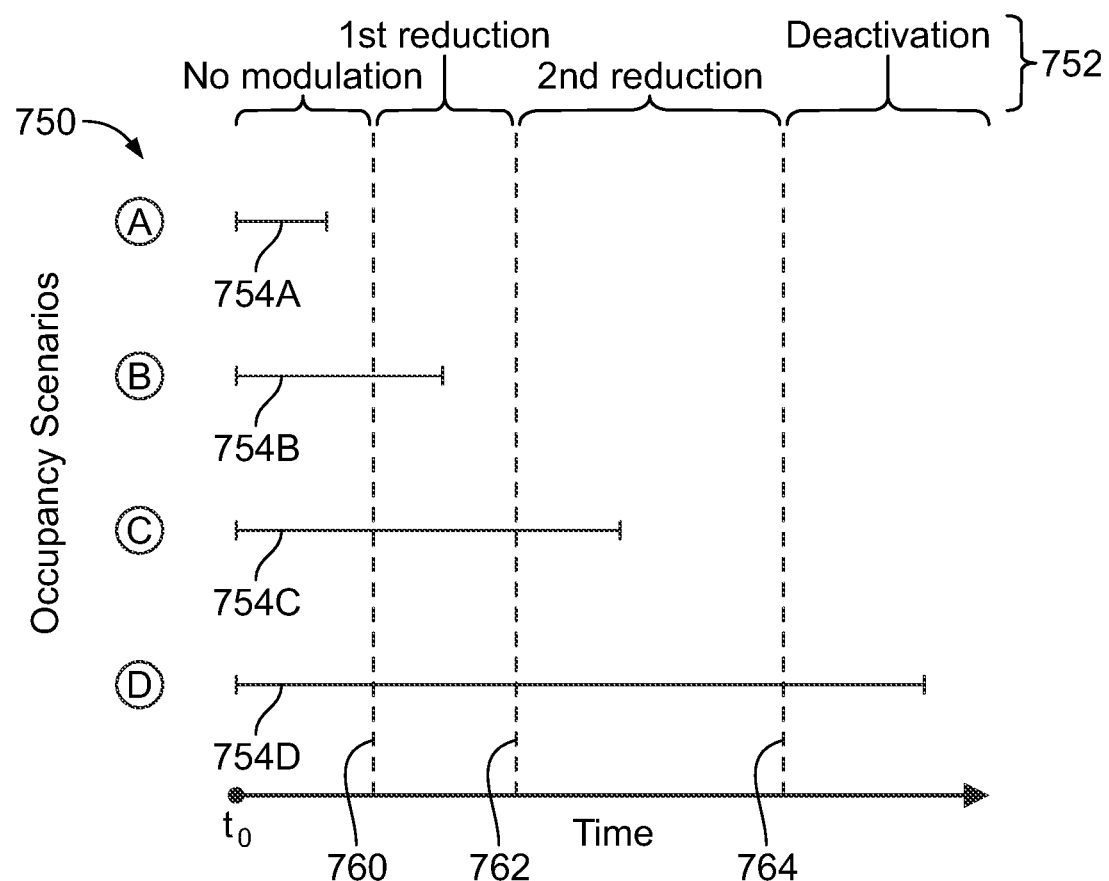
FIG. 11 is a diagram showing control operations of a sanitizing system according to multiple occupancy scenarios over time, according to an embodiment of the present disclosure.

FIG. 11 is a diagram 750 showing control operations 752 of the sanitizing system 100 according to multiple occupancy scenarios over time. The occupancy scenarios are labeled A, B, C, and D. In each scenario, occupancy of a target zone 210 monitored by the one or more occupancy sensors 102 (e.g., the IR sensor 224) is detected at time $t_0$. Each scenario includes a respective bar 754A, 754B, 754C, 754D that represents an occupancy duration (or occupancy period) in which the target zone is occupied, starting at time $t_0$. As shown, the scenarios A-D have increasing occupancy durations such that the occupancy duration in scenario A is shortest and the occupancy duration in scenario D is longest. The occupancy duration represents the time from an occupied status until an unoccupied status. For example, if the sanitizing system 100 detects that three people have entered the space during a common time period, the occupancy duration does not end until all three people have exited the space and no other people have entered the space. As described above with respect to FIGS. 1 and 2, the occupancy status of the target zone 210 (e.g., occupied or unoccupied) is determined based on the thermal image data and the reference temperature of the space.

The control operations 752 represent non-limiting, example responses of the control unit 106 to the different occupancy durations of the four scenarios. The control operations 752 and any other responsive actions undertaken by the control unit 106 may be based on programmed instructions embedded in the control logic of the processors 114 or stored in the memory 116. The control operations 752 indicate how the control unit 106 modulates the irradiance of the UV lamp 104 based on the occupancy. In each of the scenarios A-D, it is assumed that the UV lamp 104 is operating at the full irradiance level prior to the initial occupancy detection at time $t_0$. In the illustrated embodiment, the control unit 106 may compare the monitored occupancy to multiple threshold time periods, which may be predetermined and stored in the memory 116. The diagram 750 shows a first threshold time period 760, a second threshold time period 762, and a third threshold time period 764, which are indicated by dashed lines that intersect the timeline. Each of the threshold time periods 760, 762, 764 extends from time $t_0$ to the time associated with the respective dashed line, such that the first threshold time period 760 is shortest and the third threshold time period 764 is longest.

In scenario A, it is determined that the target zone is occupied, but the occupancy period 754A ends prior to the end of the first threshold time period 760. For example, a person may walk into the target zone and immediate exit the target zone, such that the occupation is transient. The occupancy duration in scenario A may be only one or a few seconds. For example, the first threshold time period 760 may be a value within a range from 1 second to 10 seconds, such as two seconds, three seconds, four seconds, five seconds, six seconds, or the like, and it is shown that the occupancy duration in scenario A is less than the first threshold time period 760. In an embodiment, in response to determining a situation as shown in scenario A, in which the target zone is occupied for a period of time that does not exceed the first threshold time period 760, the control unit 106 (e.g., the one or more processors 114 thereof) is configured to operate the UV lamp 104 to emit the UV light at the full irradiance level. For example, at such a short or transient occupation, the control unit 106 does not even adjust the power output of the UV lamp 104 because such a transient exposure to the UV light would not pose any risk of harm to the occupant or occupants within the space.

In scenario B, the occupancy period 754B exceeds the first threshold time period 760 but ends prior to the second threshold time period 762. In an embodiment, once the control unit 106 determines, based on the sensor signals, that the occupancy exceeds the first threshold time period 706, the control unit 106 controls the UV lamp 104 to reduce the irradiance of the UV light to a reduced irradiance level (e.g., a first reduced irradiance level) while continuing to emit the UV light into the target zone. The control unit 106 steps down the irradiance of the UV lamp upon crossing the first threshold time period 760. In a non-limiting example, the full irradiance level may have an irradiance of 2 $mW/cm^2$, and the first reduced irradiance level may have an irradiance of 1 $mW/cm^2$. The first reduced irradiance level may be greater than the irradiance provided by a nominal lower power setting. Optionally, after determining that the space is once again unoccupied at the end of the occupancy period 754B, the control unit 106 may increase (e.g., step up) the irradiance of the UV lamp 104 to the full irradiance level to continue disinfecting the components in the space at the desired irradiance level. The UV lamp 104 operating at the reduced irradiance level not only reduces the energy or intensity of the UV light that could impinge on an occupant relative to the full irradiance level, but also reduces the energy consumption (e.g., power draw) of the UV lamp 104. By reducing the irradiance level, the UV lamp 104 could be operated for a longer period of time between charging (e.g., charge cycles) than if the UV lamp 104 is only operated at the full irradiance level.

The occupancy period 754C in scenario C exceeds the first and the second threshold time periods 760, 762, but ends prior to the third threshold time period 764. In response to determining that the occupancy period 754C exceeds the second threshold time period 762, the control unit 106 controls the UV lamp 104 to reduce the irradiance of the UV light further to a second reduced irradiance level, while continuing to emit the UV light into the target zone. The first reduced irradiance level has greater power (e.g., greater irradiance) than the second reduced irradiance level. If the first irradiance level is the 1 $mW/cm^2$ as described in the example, above, the second irradiance level is less than 1 $mW/cm^2$, such as 0.5 $mW/cm^2$. The second threshold time period 762 may be a value within a range from three seconds to 20 seconds, such as five seconds, 10 seconds, or the like. Optionally, after determining that the space is unoccupied at the end of the occupancy period 754C, the control unit 106 may increase (e.g., step up) the irradiance of the UV lamp 104 to the full irradiance level to continue disinfecting the components in the space at the desired irradiance level.

In scenario D, the occupancy period 754D exceeds the first, second, and third threshold time periods 760, 762, 764. In response to determining, based on the sensor signals, that the occupancy period 754D exceeds the third threshold time period 764, the control unit 106 deactivates the UV lamp 104 to cease the UV lamp 104 from emitting UV light. For example, once the occupation persists longer than the third threshold time period 764, the control unit 106 turns off the UV lamp 104 entirely to halt the disinfection process. In another embodiment, instead of deactivating the UV lamp 104, the control unit 106 may step down the irradiance of the UV light again (e.g., to a level below the second reduced irradiance level) by selecting a nominal, lowest power setting for the UV lamp 104. The third threshold time period 764 may be a value within a range from 10 seconds to 40 seconds, such as 15 seconds, 20 seconds, or the like. Optionally, after determining that the space is unoccupied at the end of the occupancy period 754D, the control unit 106 may increase (e.g., step up) the irradiance of the UV lamp 104 to the full irradiance level to continue disinfecting the components in the space at the desired irradiance level.

The examples described with reference to the diagram 750 indicate that the control unit 106 may module the irradiance of the UV light based on a detected occupancy of the target zone by initially postponing any irradiance adjustment, then stepping down the irradiance one or more times before eventually deactivating the UV lamp (or operating the UV lamp at a nominal, low power settings) as the occupancy persists. The number of step-downs may vary for different embodiments. For example, although two step-downs are described in FIG. 11, in another embodiment the control unit 106 may only utilize one irradiance step-down before deactivating the UV lamp 104. In such an embodiment, either the first or second threshold time period 760, 762 may be omitted, and the third threshold time period 764 may represent a second threshold time period. The terms "first", "second", and "third" are used herein merely for identifying and differentiating the multiple thresholds that can be used by the sanitizing system 100. In another embodiment, the control unit 106 may utilize three or more irradiance step-downs before deactivating the UV lamp 104.

In one or more other embodiments, instead of discrete step-downs in UV irradiance upon occupation persisting beyond successive time thresholds, the control unit 106 may more fluidly control the UV lamp 104 to gradually reduce the irradiance over time at a designated reduction rate. For example, upon detecting that the space is occupied, the control unit 106 may control the UV lamp 104 to continuously decrease the irradiance or power output over time at the designated reduction rate until the UV lamp 104 eventually turns off, the irradiance reaches the nominal low power setting, or it is determined that the space is no longer occupied, whichever occurs first. Alternatively, instead of beginning the sliding-scale reduction of the UV irradiance immediately upon occupation, the control unit 106 may delay the irradiance reduction until after the occupation period surpasses the first threshold time period 760, as shown in FIG. 11.

In one or more embodiments, the threshold time periods and/or the irradiation levels of the UV light utilized for the control operations described above may be determined based at least in part on the wavelength or wavelength range of the UV light emitted by the UV lamp 104. In a non-limiting example, the UV lamp 104 may emit UV light at 222 nm, or at a narrow wavelength range that includes 222 nm, such as a range from 200 nm to 225 nm. This wavelength and/or narrow wavelength range may be associated with a threshold limit value (TLV), according to the American Conference of Governmental Industrial Hygienists (ACGIH).

The wavelength or narrow wavelength range of the UV light emitted from the UV lamp 104 may be controlled by the wavelength selective filter 110 (shown in FIG. 1). For example, the wavelength selective filter 110 may be specifically designed and constructed to only emit a predetermined wavelength or narrow wavelength range. In an embodiment, once the wavelength or narrow wavelength range of UV light from the UV lamp 104 is known, the control unit 106 can consult a chart to determine the TLV of the UV light. Then, the control unit 106 select other parameters for the control operations, such as the values of the reduced irradiance levels, based on the TLV of the UV light to avoid providing a germicidal dose that exceeds the TLV into an occupied space.

The TLV of the wavelength and/or narrow wavelength range according to an embodiment is sufficiently large to enable a germicidal useful dose of UV light to be delivered to an area while that area is occupied. For example, the TLV may be 23 mJ/cm$^2$, and the germicidal dose could be in a range from 2 mJ/cm$^2$ to 20 mJ/cm$^2$, such that the germicidal dose does not exceed the TLV. Controlling the wavelength of the UV light that is emitted to have a relatively high TLV that exceeds the germicidal dose allows for a useful level of irradiance to continue in a nominally occupied space. In a non-limiting example, operating a 222 nm UV lamp to illuminate an area at a low power irradiance level of 1 mW could allow for about 23 seconds of exposure before exceeding the maximum allowable exposure level. Operating the same UV lamp at a high (or full) power irradiance level of 10 mW could allow for 2.3 seconds of exposure before exceeding the maximum allowable exposure level. As a result, the control unit 106 may set the first threshold time period 760 in FIG. 11 to be a value less than 2.3 seconds, such as 2 seconds, to avoid exceeding the allowable UV exposure level or dose. By understanding the exposure levels of the UV light, the sanitizing system 100 can provide for continued emission of UV light at a fairly high power into the space after detecting that the space is occupied, although only for a short, transient amount of time. By initially postponing the irradiance reduction, the sanitizing system 100 can provide enhanced disinfection of a nominally occupied area relative to immediately deactivating the UV upon detecting occupancy. If the UV lamp 104 is stepped down, due to persistent occupation of the space, to the low power irradiance level of 1 mW, a subsequent threshold time period may be set to a value less than 23 seconds, such as 20 seconds, to avoid exceeding the allowable UV exposure level or dose. It is noted that the TLV value of 23 mJ/cm$^2$ for 222 nm UV light is provided for example, and the actual TLV value of 222 nm UV light may be different, such as greater than 23 mJ/cm$^2$.

The control unit 106 according to one or more embodiments may determine periodic occupancy trends for the target zone, and may utilize the periodic occupancy trends to modulate the irradiance of the UV light that is emitted by the UV lamp 104 over time. Unlike the control operations 752 shown and described with reference to FIG. 11 that are based on real-time occupancy data of the target zone, the control unit 106 may also analyze historical occupancy data associated with the target zone and/or similar spaces in similar, but different, vehicles or buildings. For example, the historical occupancy data may include all of the sensor signals generated by the occupancy sensor or sensors 102 that monitor the target zone over a previous extended time period, such as the prior month or year. The one or more processors 114 of the control unit 106 may analyze the historical occupancy data to determine the periodic occupancy trends for the target zone. The periodic occupancy trends may indicate cyclic occupancy patterns within the target zone, including a level of deviation from the patterns. The periodic occupancy trends may identify certain time periods during each day or week in which the target zone is typically unoccupied and other time periods during the day or week in which the target zone is typically occupied. For example, on Mondays, the target zone is typically unoccupied for an hour from 7 AM to 8 AM. The periodic occupancy trends may also indicate the density of occupancy, such as the expected amount of people within the target zone at different times of the day or week.

In an embodiment, at least one of the one or more processors 114 may represent or include a prediction module or feature that utilizes data analysis, machine learning, and/or artificial intelligence (AI). The prediction module may analyze historical data representing the occupancy of the target zone over time to "learn" and generate occupancy trends. The occupancy trends may indicate the frequency that people pass through the space over an extended period of time, such as a day, a week, a month, a year, or the like. The prediction module may use the occupancy trends to predict upcoming occupancy cycles or periods prior to actual detection by the occupancy sensor. The control unit may adjust the irradiance of the UV light based on the predicted upcoming occupancy cycles to reach a balance between providing sufficient UV dosage for disinfection without risking harm to people within the space.

By analyzing the historical data, the prediction module may "learn" how the target zone is typically occupied, and then modulate the irradiance of the UV light based on the learned occupancy trends. Optionally, the prediction module may correlate the historical occupancy data of the target zone with historical (e.g., past) schedules, such as trip schedules in the case of the space being within a commercial vehicle. The prediction module can "learn" or identify how the occupancy of the space correlates with the schedules. For example, if a trip is scheduled to begin at 6 AM and the vehicle has been stationary for at least a few hours, the data may indicate that the space is occupied by a cleaning crew one hour prior to the departure time, and then is unoccupied for a certain interval of time until the trip crew occupies the space 30 minutes prior to the departure. Using this information, the control unit 106 can schedule a disinfection process by the UV lamp 104 to occur within the interval between the cleaning crew exiting the space and the trip crew entering the space. Depending on the duration of this interval within the periodic occupancy trends, the control unit 106 may adjust one or more settings of the disinfection process. For example, if the interval is relatively short, then the control unit 106 can increase the power to the UV lamp to increase the full irradiance level of the UV light. As a result of the increased irradiance, the control unit 106 may also shorten one or more of the threshold time periods 760, 762, 764 in FIG. 11 to avoid excess UV exposure to any persons that enter the space during the disinfection process. Such adjustment of the disinfection start time, duration, UV irradiance, and threshold time periods based on the periodic occupancy trends can be used to provide efficient disinfection of the components within the target zone and ensure safety of any person that enters the target zone during the disinfection process.

Figure 12:
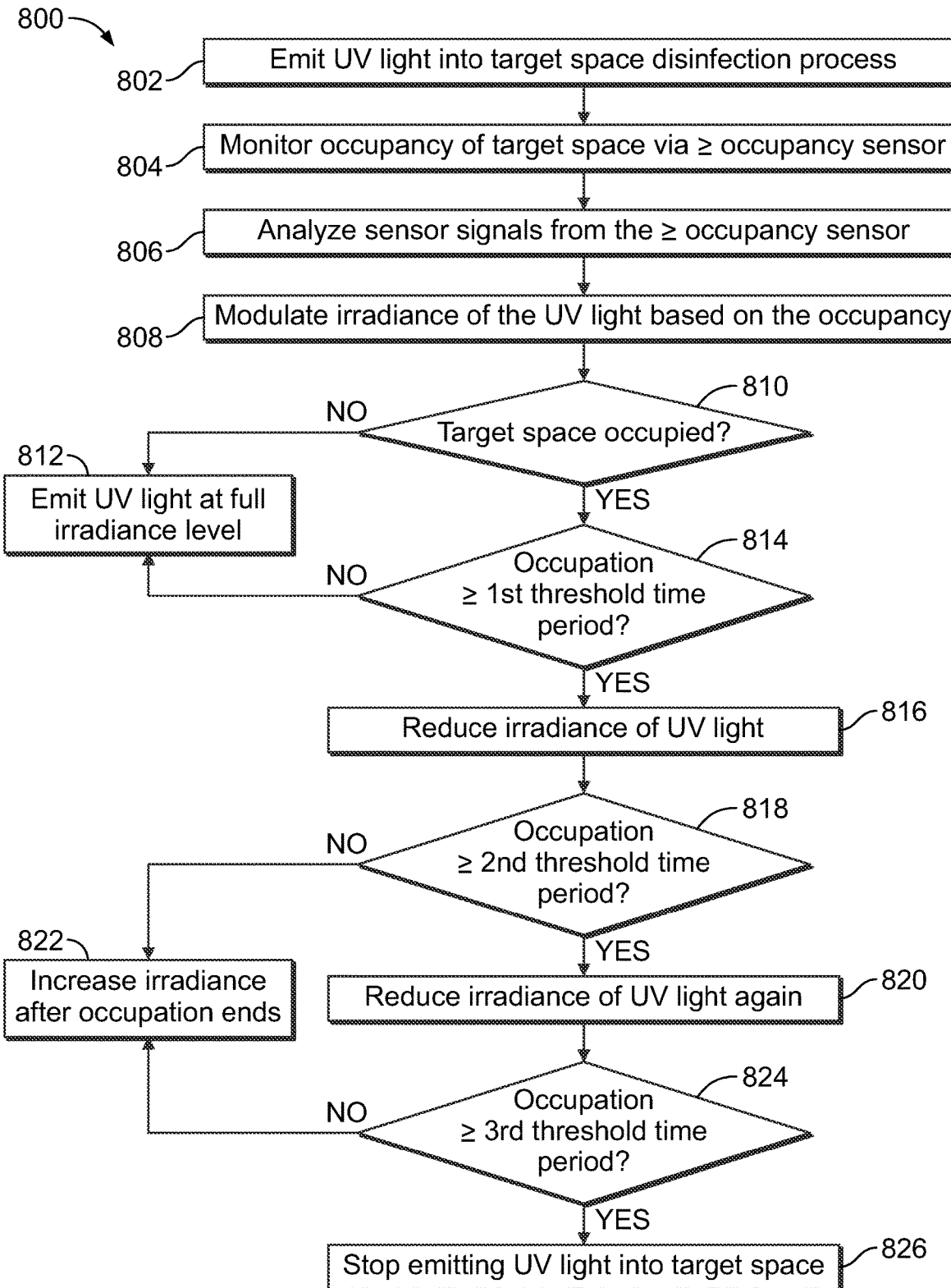
FIG. 12 illustrates a flow chart of a sanitizing method, according to an embodiment of the present disclosure.

FIG. 12 illustrates a flow chart 800 of a sanitizing method according to an embodiment of the present disclosure. Referring to FIGS. 1 through 12, the method begins at 802, at which the UV light is emitted into a target zone for a disinfection process. The UV light is directed towards one or more components in the target zone to neutralize pathogens on the components and/or in the air. The UV light is generated by at least one UV lamp 104. The target zone may be a region within an enclosed space, such as a room within a commercial vehicle or a building.

At 804, the target zone is monitored via one or more occupancy sensors 102 that are configured to generate sensor signals over time indicative of an occupancy of the target zone. As described above with respect to FIGS. 1 and 2, the occupancy status of the target zone is determined based on the thermal image data and the reference temperature of the space. At 806, the sensor signals from the one or more occupancy sensors 102 are analyzed via a control unit 106 that comprises one or more processors 114. At 808, an irradiance of the UV light that is emitted into the target zone is modulated, over time, based on the occupancy of the target zone. The control unit 106 may control the modulation of the UV light that is emitted by the UV lamp 104 by generating control signals that are communicated to the UV lamp 104.

The following steps and operations of the method describe how the irradiance of the UV light may be monitored. At 810, it is determined, by the control unit 106, whether the target zone is occupied. If the target zone is determined to be unoccupied, the method proceeds to 812, and the UV light is emitted into the target zone at a full irradiance level, which may represent a full power or high power setting. If, on the other hand, the target zone is determined to be occupied at 810, then flow proceeds to 814 where a determination is made, by the control unit 106, whether the occupation of the target zone persists for at least as long as a first threshold time period 760. If not, then flow returns to 812 and the UV light continues to be emitted at the full irradiance level. On the other hand, if the occupation persists for at least as the first threshold time period 760, then the method proceeds to 816. At 816, the irradiance of the UV light is reduced, such as to a first reduced irradiance level.

At 818, it is determined, by the control unit 106, whether the occupation of the target zone persists for at least as long as a second threshold time period 762 (which is longer than the first threshold time period 760). If not, once the occupation is determined to be over, such that the space is once again unoccupied, the irradiance of the UV light is increased at 822. The UV irradiance may be increased back to the full irradiance level. If, on the other hand, the occupation persists for at least as long as the second threshold time period 762, the method proceeds to 820 and the irradiance of the UV light is reduced again (e.g., a second time) to an irradiance level below the previous irradiance level. Even at the second reduced irradiance level, the UV light may have an irradiance that is greater than a nominal or lower limit irradiance level. From 820 the method proceeds to 824 and it is determined, by the control unit 106, whether the occupation of the target zone persists for at least as long as a third threshold time period 764 (which is longer than the second threshold time period 762). If not, once the occupation is determined to be over, such that the space is once again unoccupied, the irradiance of the UV light is increased at 822. If, on the other hand, the occupation persists for at least as long as the third threshold time period 764, the method proceeds to 826 and the UV light is stopped from further emission into the target zone. For example, the control unit 106 may deactivate or turn off the UV lamp 104.

Figure 13:
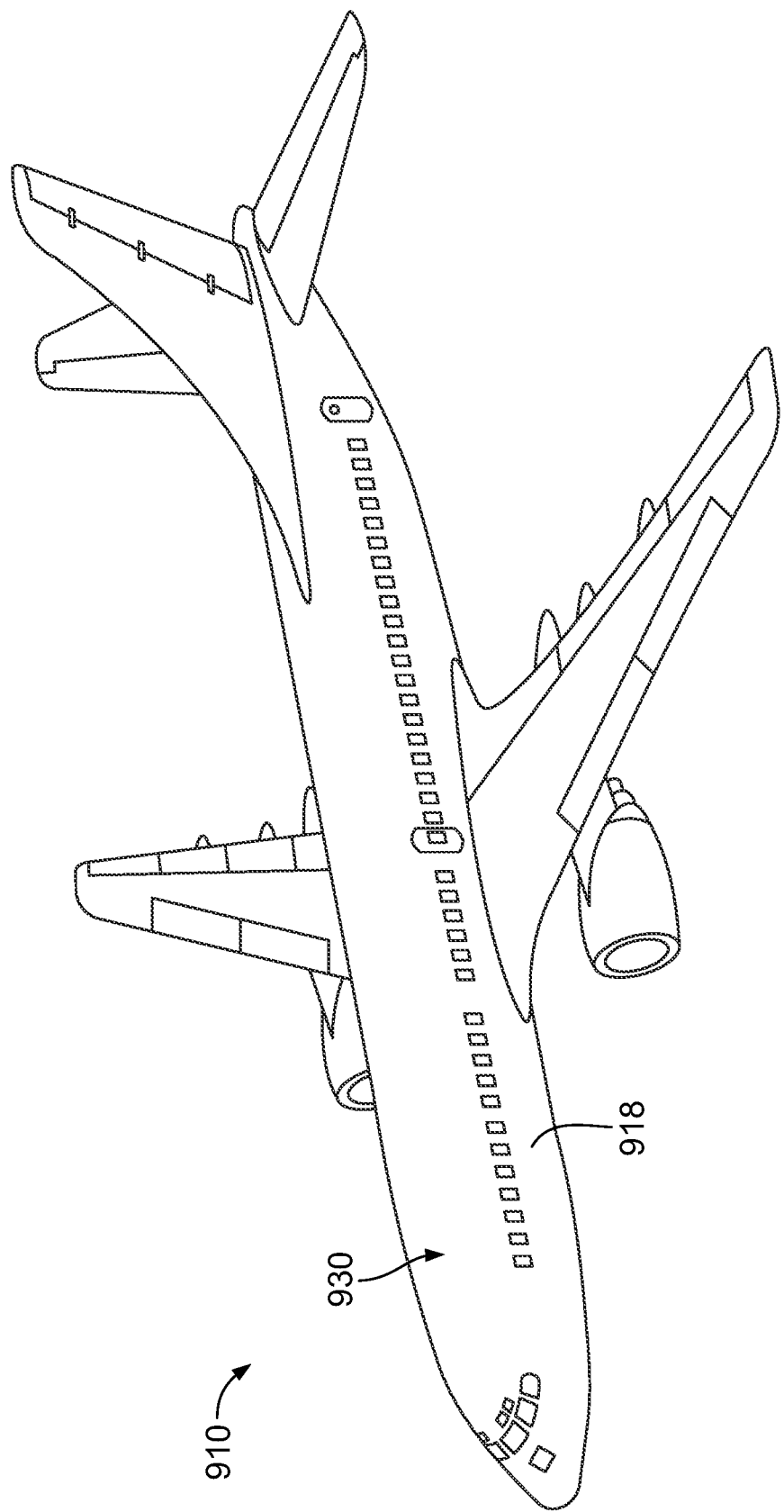
FIG. 13 illustrates a perspective top view of an aircraft, according to an embodiment of the present disclosure.

FIG. 13 illustrates a perspective top view of an aircraft 910, according to an embodiment of the present disclosure. The aircraft 910 includes a fuselage 918. The fuselage 918 of the aircraft 910 defines an internal cabin 930, which may include a cockpit, one or more work sections (for example, galleys, personnel carry-on baggage areas, and the like), one or more passenger sections (for example, first class, business class, and coach sections), and an aft section in which an aft rest area assembly may be positioned. The internal cabin 930 includes one or more lavatories, for example, the lavatories 1010 shown in FIG. 14.

While various embodiments are discussed in connection with aircraft, it may be again noted that other embodiments may be utilized in connection with, for example, other vehicle, such as ships, or ground-based vehicles such as buses or trains. Alternatively, instead of an aircraft, embodiments of the present disclosure may be used with various other vehicles, such as automobiles, buses, locomotives and train cars, watercraft, spacecraft, and the like. Further, embodiments of the present disclosure may be used with respect to fixed structures, such as commercial and residential buildings.

Figure 14:
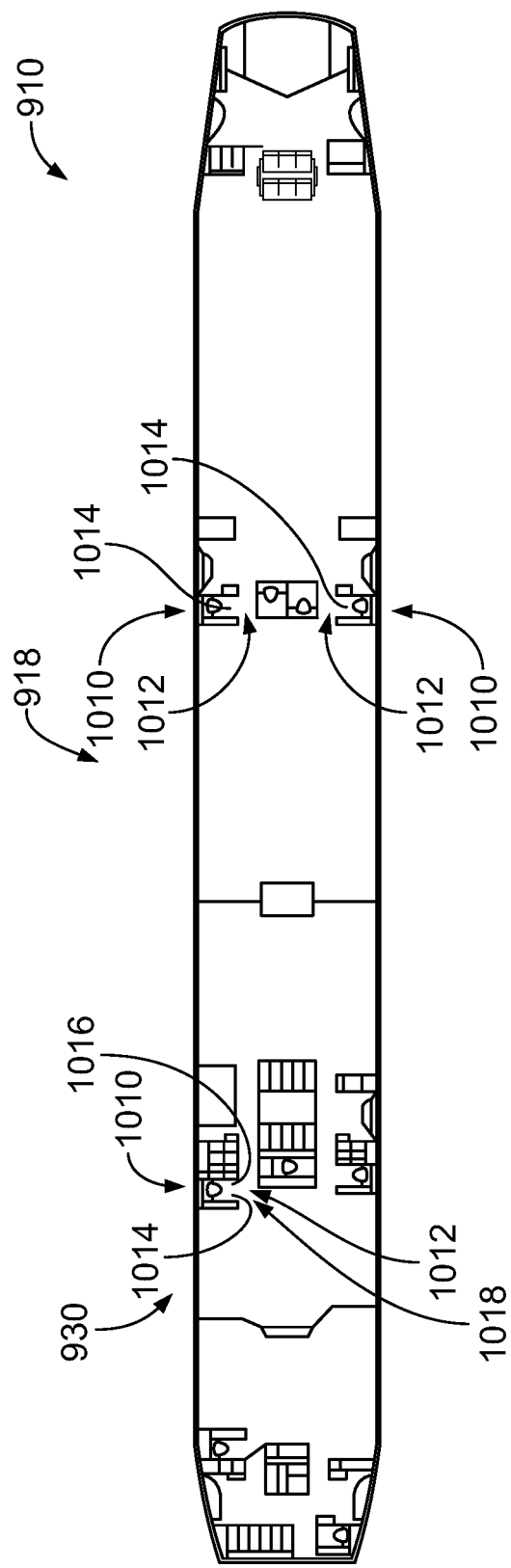
FIG. 14 illustrates a top plan view of an internal cabin of the aircraft, according to an embodiment of the present disclosure.

FIG. 14 illustrates a top plan view of the internal cabin 930 of the aircraft 910, according to an embodiment of the present disclosure. One or more lavatories 1010 may be located within the internal cabin 930. Each lavatory 1010 includes a lavatory floor 1012. The lavatories 1010 may include floor assemblies (e.g., floor assembly 1014) as discussed herein, which may be secured within a portion of the fuselage. The floor assembly 1014 is configured to form a portion of a floor 1016 (e.g., lavatory floor 1012) in an enclosed space 1018 (e.g., aircraft lavatory, ship lavatory, or lavatory of ground-based vehicles such as buses or trains), or to be positioned on or in a floor 1015 of an enclosed space 1018.

Embodiments of the present disclosure are used to disinfect various components within a space, such as the enclosed space 1018 in the internal cabin 530. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 15:
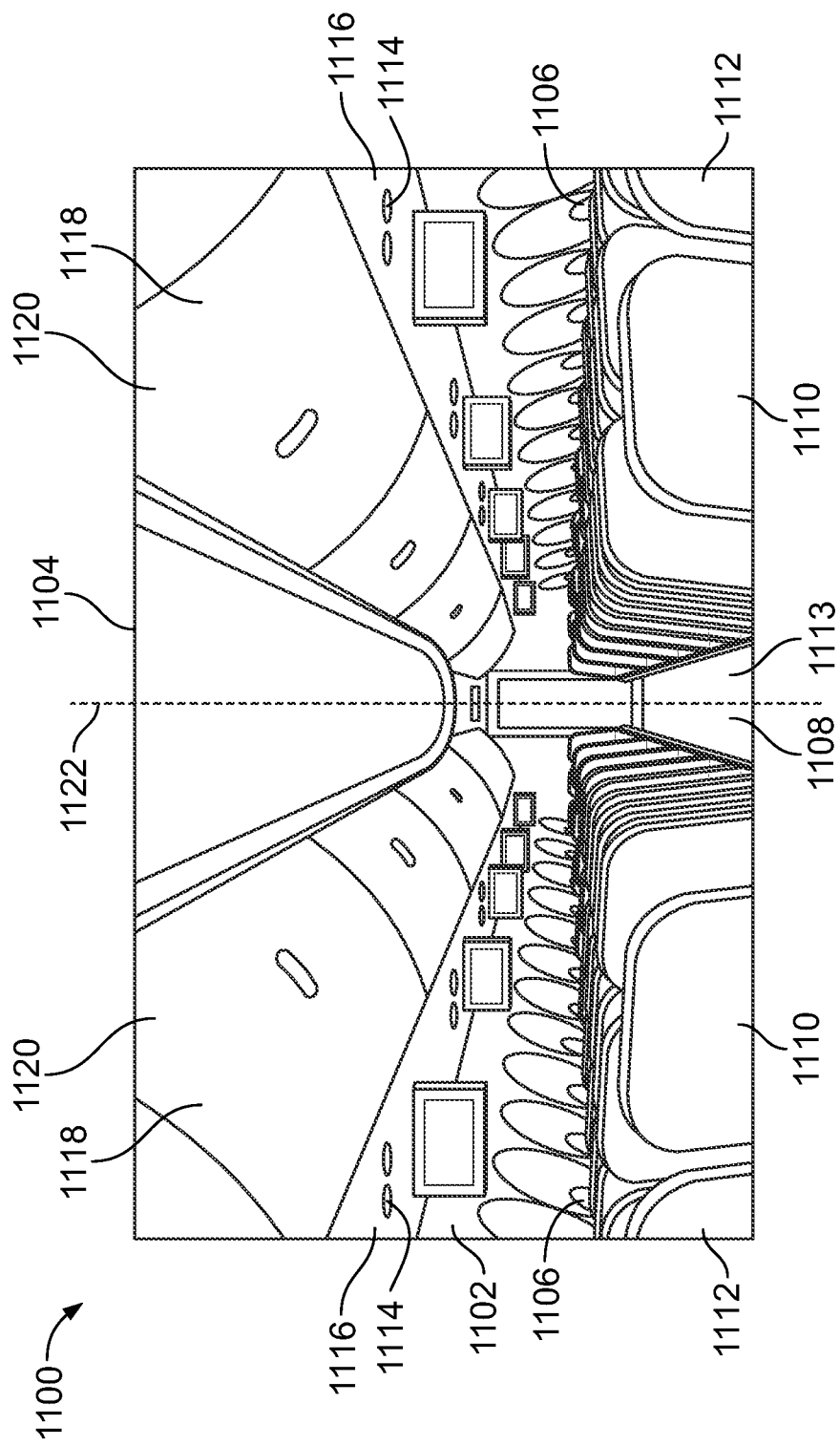
FIG. 15 illustrates a perspective interior view of an internal cabin of an aircraft, according to an embodiment of the present disclosure.

FIG. 15 illustrates a perspective interior view of an internal cabin 1100 of an aircraft, according to an embodiment of the present disclosure. The internal cabin 1100 includes outboard walls 1102 connected to a ceiling 1104. Windows 1106 may be formed within the outboard walls

1102. A floor 1108 supports rows of seats 1110. As shown in FIG. 8, a row 1112 may include two seats 1110 on either side of an aisle 1113. However, the row 1112 may include more or less seats 1110 than shown. Additionally, the internal cabin 1100 may include more aisles than shown.

Passenger service units (PSUs) 1114 are secured between an outboard wall 1102 and the ceiling 1104 on either side of the aisle 1113. The PSUs 1114 extend between a front end and rear end of the internal cabin 1100. For example, a PSU 1114 may be positioned over each seat 1110 within a row 1112. Each PSU 1114 may include a housing 1116 that generally contains vents, reading lights, an oxygen bag drop panel, an attendant request button, and other such controls over each seat 1110 (or groups of seats) within a row 1112.

Overhead stowage bin assemblies 1118 are secured to the ceiling 1104 and/or the outboard wall 1102 above and inboard from the PSU 1114 on either side of the aisle 1113. The overhead stowage bin assemblies 1118 are secured over the seats 1110. The overhead stowage bin assemblies 1118 extend between the front and rear end of the internal cabin 1100. Each stowage bin assembly 1118 may include a pivot bin or bucket 1120 pivotally secured to a strongback (hidden from view in FIG. 15). The overhead stowage bin assemblies 1118 may be positioned above and inboard from lower surfaces of the PSUs 1114. The overhead stowage bin assemblies 1118 are configured to be pivoted open in order to receive passenger carry-on baggage and personal items, for example. Embodiments of the present disclosure shown and described with respect to FIGS. 1-5 may be used to sanitize various structures shown within the internal cabin 1100, such as the passenger seats 1110, monuments, stowage bin assemblies 1118, components on and within lavatories, galley equipment and components, and/or the like.

As used herein, the term "outboard" means a position that is further away from a central longitudinal plane 1122 of the internal cabin 1100 as compared to another component. The term "inboard" means a position that is closer to the central longitudinal plane 1122 of the internal cabin 1100 as compared to another component. For example, a lower surface of a PSU 1114 may be outboard in relation to a stowage bin assembly 1118.

As described herein, certain embodiments of the present disclosure provide systems and methods that allow for efficient disinfection of a target zone or room even when the space or room is occasionally occupied. Further, certain embodiments of the present disclosure provide systems and methods that accurately and reliable detect the presence of one or more people within a space to which one or more UV lamps are directed, even if the environment is static for an extended period of time. Further, certain embodiments of the present disclosure provide systems and methods that modulate the irradiance of emitted UV light to ensure that the UV dosage applied to people occupying the space or room is safe (e.g., less than a maximum allowable UV dosage).

Further, the disclosure comprises embodiments according to the following clauses:

Clause 1. A sanitizing system comprising:
an infrared (IR) sensor configured to generate thermal image data of a target zone within a space;
a control unit including one or more processors and communicatively connected to the IR sensor, the control unit configured to determine an occupancy status of the target zone based on the thermal image data and a reference temperature of the space; and
one or more ultraviolet (UV) lamps communicatively connected to the control unit, each of the one or more UV lamps configured to emit UV light into the target zone, wherein the control unit is configured to operate the one or more UV lamps based on the determined occupancy status of the target zone.

Clause 2. The sanitizing system of Clause 1, wherein the thermal image data generated by the IR sensor indicates an absolute temperature of one or more components disposed within the target zone, wherein the control unit is configured to (i) determine a threshold temperature based on the reference temperature of the space and (ii) determine the occupancy status by comparing the absolute temperature of the one or more components to the threshold temperature.

Clause 3. The sanitizing system of Clause 2, wherein the control unit is configured to determine that the target zone is occupied by at least one person in response to the absolute temperature exceeding the threshold temperature.

Clause 4. The sanitizing system of Clause 2 or Clause 3, wherein the control unit is configured to determine the threshold temperature as a function of the reference temperature.

Clause 5. The sanitizing system of any of Clauses 2-4, wherein the control unit is configured to modulate the threshold temperature in response to a change in the reference temperature.

Clause 6. The sanitizing system of Clause 5, wherein the control unit is configured to one or both of (i) lower the threshold temperature in response to a drop in the reference temperature, or (ii) increase the threshold temperature in response to a rise in the reference temperature Clause 7. The sanitizing system of any of Clauses 1-6, wherein the IR sensor is positioned and oriented such that a field of view of the IR sensor encompasses both (i) the target zone and (ii) a non-target zone that is designated as unoccupied, wherein the IR sensor is configured to also generate thermal image data of the non-target zone, and the control unit is configured to analyze the thermal image data of the non-target zone to determine the reference temperature of the space.

Clause 8. The sanitizing system of Clause 7, wherein the IR sensor comprises an array of pixels, where a first subset of pixels in the array is directed at the target zone and a second subset of pixels in the array is directed at the non-target zone.

Clause 9. The sanitizing system of any of Clauses 1-6, further comprising a second sensor communicatively connected to the control unit, the second sensor configured to generate sensor signals indicative of the reference temperature of the space.

Clause 10. The sanitizing system of Clause 9, wherein the second sensor is a second IR sensor oriented to generate thermal image data of a non-target zone that is predetermined to be unoccupied.

Clause 11. The sanitizing system of any of Clauses 1-10, wherein, in response to the occupancy status indicating that the target zone is occupied while the one or more UV lamps are active, the control unit is configured to operate the one or more UV lamps to one or more of (i) stop emitting the UV light or (ii) reduce an output level of the one or more UV lamps.

Clause 12. The sanitizing system of any of Clauses 1-11, wherein, when the one or more UV lamps are inactive, the control unit is configured to maintain the one or more UV lamps as inactive until after the occupancy status indicates that the target zone is unoccupied.

Clause 13. The sanitizing system of any of Clauses 1-12, wherein the IR sensor is a first IR sensor and the sanitizing system further comprises a second IR sensor that is communicatively connected to the control unit and configured to generate second thermal image data of the target zone,
wherein the second IR sensor is spaced apart from the first IR sensor and oriented such that a field of view of the second IR sensor overlaps a field of view of the first IR sensor, and wherein the control unit is configured to analyze both the thermal image data and the second thermal image data to determine the occupancy status of the target zone.

Clause 14. The sanitizing system of Clause 13, wherein the IR sensor comprises an array of pixels, wherein a field of view of at least some pixels in the array overlap with a field of view of at least some pixels of the second IR sensor, and the control unit is configured to determine a location, within the target zone, of one or more components present in an overlapping region of the two fields of view.

Clause 15. The sanitizing system of any of Clauses 1-14, wherein the control unit is configured to aggregate the thermal image data that is generated by the IR sensor over time to determine a baseline temperature profile for the target zone, and to determine the occupancy status based at least in part on the baseline temperature profile.

Clause 16. The sanitizing system of any of Clauses 1-15, wherein the IR sensor comprises multiple pixels in an array, the pixels positioned to monitor different areas of the target zone relative to one another, wherein the control unit is configured to determine a respective baseline temperature profile for each of the different areas monitored by the different pixels, and to determine the occupancy status based at least in part on the respective baseline temperature profile of one or more of the different areas.

Clause 17. The sanitizing system of any of Clauses 1-16, wherein the IR sensor comprises multiple pixels in an array, the pixels configured to generate different portions of the thermal image data corresponding to different monitored areas of the target zone, wherein the control unit is configured to determine an individual occupancy status for each of the monitored areas of the target zone to determine the occupancy status of the target zone.

Clause 18. The sanitizing system of any of Clauses 1-17, wherein the one or more UV lamps and the IR sensor are mounted within one or more rooms, and the UV light emitted by the one or more UV lamps is configured to disinfect components located within the one or more rooms.

Clause 19. The sanitizing system of Clause 18, wherein the one or more rooms are within a vehicle.

Clause 20. The sanitizing system of Clause 19, wherein the one or more rooms within the vehicle include one or more of a lavatory, a lavatory waiting area, a galley, a passenger seating area, a hallway, a flight deck, a cargo area, or a rest area.

Clause 21. The sanitizing system of any of Clauses 1-20, wherein the reference temperature of the space is an ambient temperature of the space.

Clause 22. The sanitizing system of any of Clauses 1-21, wherein the reference temperature of the space is an absolute temperature of an object in a non-target zone within the space, wherein the non-target zone is adjacent to the target zone, has a similar ambient temperature profile as the target zone, and is predetermined to be unoccupied.

Clause 23. A method comprising:
receiving, at a control unit including one or more processors, thermal image data generated by an infrared (IR) sensor and associated with a target zone within a space;
determining, via the control unit, an occupancy status of the target zone based on the thermal image data and a reference temperature of the space; and
operating one or more ultraviolet (UV) lamps, via the control unit, based on the occupancy status of the target zone, the one or more UV lamps configured to emit UV light into the target zone.

Clause 24. The method of Clause 23, wherein the thermal image data generated by the IR sensor indicates an absolute temperature of one or more components disposed within the target zone, and the method further comprises:
determining a threshold temperature based on the reference temperature of the space, and wherein determining the occupancy status of the target zone based on the thermal image data and the reference temperature of the space comprises comparing the absolute temperature of the one or more components to the threshold temperature.

Clause 25. The method of Clause 24, wherein determining the occupancy status includes determining that the target zone is occupied by at least one person in response to the reference temperature exceeding the threshold temperature.

Clause 26. The method of any of Clauses 23-25, wherein the method further comprises determining the reference temperature of the space, wherein the reference temperature is determined based on second thermal image data generated by (i) the IR sensor or (ii) a second IR sensor, the second thermal image data associated with a non-target zone that is designated as unoccupied.

Clause 27. The method of any of Clauses 23-26, wherein operating the one or more UV lamps based on the occupancy status includes, when the one or more UV lamps are active and the occupancy status indicates that the target zone is occupied, one or more of (i) deactivating the UV lamps to stop emitting the UV light or (ii) reducing an output level of the one or more UV lamps.

Clause 28. The method of any of Clauses 23-27, wherein operating the one or more UV lamps based on the occupancy status includes, when the one or more UV lamps are inactive, maintaining the one or more UV lamps as inactive until after the occupancy status indicates that the target zone is unoccupied.

Clause 29. A sanitizing system comprising:
an infrared (IR) sensor configured to generate thermal image data of a target zone within a space, the IR sensor calibrated such that the thermal image data indicates an absolute temperature of one or more components in the target zone;
a control unit including one or more processors and communicatively connected to the IR sensor, the control unit configured to (i) determine an ambient temperature of the space based on sensor data generated by the IR sensor or a second sensor, (ii) determine a threshold temperature based on the ambient temperature of the space, and (iii) determine an occupancy status of the target zone by comparing the absolute temperature of the one or more components to the threshold temperature; and
one or more ultraviolet (UV) lamps communicatively connected to the control unit, each of the one or more UV lamps configured to emit UV light into the target zone, wherein the control unit is configured to operate the one or more UV lamps based on the occupancy status of the target zone.

Clause 30. The sanitizing system of Clause 29, wherein, in response to the occupancy status indicating that the target zone is occupied while the one or more UV lamps are active, the control unit is configured to operate the one or more UV lamps to one or more of (i) stop emitting the UV light or (ii) reduce an output level of the one or more UV lamps.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system comprising:
    an infrared (IR) sensor configured to generate thermal image data of a target zone within a space;
    a control unit including one or more processors and communicatively connected to the IR sensor, the control unit configured to determine an occupancy status of the target zone based on the thermal image data and a reference temperature of the space; and
    one or more ultraviolet (UV) lamps communicatively connected to the control unit, wherein the control unit is configured to operate the one or more UV lamps to emit UV light into the target zone for sanitizing one or more components within the target zone based on the determined occupancy status, wherein responsive to determining that the target zone is occupied for at least a first threshold time period while the one or more UV lamps are sanitizing the one or more components, the control unit is configured to control the one or more UV lamps to at least one of (i) stop emitting the UV light or (ii) reduce an output level of the UV light that is emitted.

2. The sanitizing system of claim 1, wherein the thermal image data generated by the IR sensor indicates an absolute temperature of the one or more components within the target zone, wherein the control unit is configured to (i) determine a threshold temperature based on the reference temperature of the space and (ii) determine the occupancy status by comparing the absolute temperature of the one or more components to the threshold temperature.

3. The sanitizing system of claim 2, wherein the control unit is configured to determine that the target zone is occupied by at least one person in response to the absolute temperature exceeding the threshold temperature.

4. The sanitizing system of claim 2, wherein the control unit is configured to modulate the threshold temperature in response to a change in the reference temperature.

5. The sanitizing system of claim 4, wherein the control unit is configured to one or both of (i) lower the threshold temperature in response to a drop in the reference temperature, or (ii) increase the threshold temperature in response to a rise in the reference temperature.

6. The sanitizing system of claim 1, wherein the IR sensor is positioned and oriented such that a field of view of the IR sensor encompasses both (i) the target zone and (ii) a non-target zone that is designated as unoccupied, wherein the IR sensor is configured to also generate thermal image data of the non-target zone, and the control unit is configured to analyze the thermal image data of the non-target zone to determine the reference temperature of the space.

7. The sanitizing system of claim 6, wherein the IR sensor comprises an array of pixels, where a first subset of pixels in the array is directed at the target zone and a second subset of pixels in the array is directed at the non-target zone.

8. The sanitizing system of claim 1, further comprising a second sensor communicatively connected to the control unit, the second sensor configured to generate sensor signals indicative of the reference temperature of the space.

9. The sanitizing system of claim 8, wherein the second sensor is a second IR sensor oriented to generate thermal image data of a non-target zone that is predetermined to be unoccupied.

10. The sanitizing system of claim 1, wherein, responsive to determining that the target zone is occupied while the one or more UV lamps are inactive, the control unit is configured to maintain the one or more UV lamps as inactive at least until the control unit determines that the target zone is unoccupied.

11. The sanitizing system of claim 1, wherein the IR sensor is a first IR sensor and the sanitizing system further comprises a second IR sensor that is communicatively connected to the control unit and configured to generate second thermal image data of the target zone,
    wherein the second IR sensor is spaced apart from the first IR sensor and oriented such that a field of view of the second IR sensor overlaps a field of view of the first IR sensor, and wherein the control unit is configured to analyze both the thermal image data and the second thermal image data to determine the occupancy status of the target zone.

12. The sanitizing system of claim 11, wherein the IR sensor comprises an array of pixels, wherein a field of view of at least some pixels in the array of pixels overlaps with a field of view of at least some pixels of the second IR sensor, and the control unit is configured to determine a location, within the target zone, of the one or more components that are present in an overlapping region of the two fields of view.

13. The sanitizing system of claim 1, wherein the control unit is configured to aggregate the thermal image data that is generated by the IR sensor over time to determine a baseline temperature profile for the target zone, and to determine the occupancy status based at least in part on the baseline temperature profile.

14. The sanitizing system of claim 1, wherein the IR sensor comprises pixels in an array, the pixels positioned to monitor different areas of the target zone relative to one another, wherein the control unit is configured to determine a respective baseline temperature profile for each of the different areas monitored by the different pixels, and to determine the occupancy status based at least in part on the respective baseline temperature profile of one or more of the different areas.

15. The sanitizing system of claim 1, wherein the IR sensor comprises pixels in an array, the pixels configured to generate different portions of the thermal image data corresponding to different monitored areas of the target zone, wherein the control unit is configured to determine an individual occupancy status for each of the different monitored areas of the target zone to determine the occupancy status of the target zone.

16. The sanitizing system of claim 1, wherein the one or more UV lamps and the IR sensor are mounted within one or more rooms, and the UV light emitted by the one or more UV lamps is configured to sanitize the one or more components that are located within the one or more rooms.

17. The sanitizing system of claim 1, wherein the control unit is configured to operate the one or more UV lamps to emit the UV light into the target zone at a wavelength range that includes 222 nm for sanitizing the one or more components within the target zone.

18. A method comprising:
receiving, at a control unit including one or more processors, thermal image data generated by an infrared (IR) sensor and associated with a target zone within a space;
determining, via the control unit, an occupancy status of the target zone based on the thermal image data and a reference temperature of the space; and
operating one or more ultraviolet (UV) lamps, via the control unit and based on the occupancy status, to emit UV light into the target zone to sanitize one or more components within the target zone, wherein operating the one or more UV lamps comprises controlling the one or more UV lamps to at least one of (i) stop emitting the UV light or (ii) reduce an output level of the UV light that is emitted in response to determining that the target zone is occupied for at least a first threshold time period while the one or more UV lamps are sanitizing the one or more components.

19. The method of claim 18, wherein the thermal image data generated by the IR sensor indicates an absolute temperature of the one or more components within the target zone, and the method further comprises:
determining a threshold temperature based on the reference temperature of the space, and wherein determining the occupancy status of the target zone based on the thermal image data and the reference temperature of the space comprises comparing the absolute temperature of the one or more components to the threshold temperature.

20. A sanitizing system comprising:
an infrared (IR) sensor configured to generate thermal image data of a target zone within a space, the IR sensor calibrated such that the thermal image data indicates an absolute temperature of one or more components in the target zone;
a control unit including one or more processors and communicatively connected to the IR sensor, the control unit configured to (i) determine an ambient temperature of the space based on sensor data generated by the IR sensor or a second sensor, (ii) determine a threshold temperature based on the ambient temperature of the space, and (iii) determine an occupancy status of the target zone by comparing the absolute temperature of the one or more components to the threshold temperature; and
one or more ultraviolet (UV) lamps communicatively connected to the control unit, wherein the control unit is configured to operate the one or more UV lamps based on the occupancy status to emit UV light to sanitize the one or more components within the target zone,
wherein in response to the control unit determining that the target zone is occupied while the one or more UV lamps are inactive, the control unit is configured to not activate the one or more UV lamps to emit the UV light into the target zone until the occupancy status indicates that the target zone is unoccupied.

* * * * *